(12) United States Patent
Davis et al.

(10) Patent No.: US 7,355,074 B2
(45) Date of Patent: Apr. 8, 2008

(54) COMPOUNDS HAVING AROMATIC RINGS AND SIDE-CHAIN AMIDE-FUNCTIONALITY AND A METHOD FOR TRANSPORTING MONOVALENT ANIONS ACROSS BIOLOGICAL MEMBRANES USING THE SAME

(75) Inventors: Jeffery T. Davis, College Park, MD (US); Vladimir Sidorov, Richmond, VA (US); Frank W. Kotch, New Phila., PA (US)

(73) Assignee: The University of Maryland, College Park, MD (US)

( * ) Notice: Subject to any disclaimer, the term of this patent is extended or adjusted under 35 U.S.C. 154(b) by 0 days.

(21) Appl. No.: 10/771,414

(22) Filed: Feb. 5, 2004

(65) Prior Publication Data

US 2005/0009921 A1 Jan. 13, 2005

Related U.S. Application Data

(60) Provisional application No. 60/445,160, filed on Feb. 5, 2003.

(51) Int. Cl.
*C07C 233/05* (2006.01)
*A61M 15/00* (2006.01)
*A61K 31/65* (2006.01)

(52) U.S. Cl. .................. 564/153; 514/616; 530/328; 128/203.12; 261/DIG. 65

(58) Field of Classification Search ............. 564/153; 514/616; 530/328; 128/203.12; 261/DIG. 65
See application file for complete search history.

(56) References Cited

U.S. PATENT DOCUMENTS 5,489,612 A * 2/1996 Atwood et al. ............ 514/569

OTHER PUBLICATIONS

Sidorov et al, J. Am. Chem. Soc., vol. 124, No. 10, pp. 2267-2278, 2002.*
Rivas et al, Proc. Nat. Acad. Sciences, vol. 98, No. 17, pp. 9478-9483, 2001.*
Sidorov et al, Chemical Commun., 2000, 2369-2370.*
Pellizzi et al, J. Chem. Soc., Perkin Trans. 2, 1998, 1307-1311.*
Sidorove et al, IT 325145-46-8P, 2000(see p. 42).*
Sidorov et al, Casonline, , pp. 36-42, 2000.*
Vladimir Sidorov, et al., "Chloride Anion Transport Across a Lipid Bilayer by an Acyclic Triamide", Dept. of Chemistry and Biochemistry, University of Md., Oct. 31, 2002, pp. 4-5.
Paul H. Schlesinger, et al., "SCMTR: A Chloride-Selective, Membrane-Anchored Peptide Channel that Exhibits Voltage Gating", J.Am. Chem. Soc., 2001, pp. 6-7.
Vladimir Sidorov, et al., "Ion Channel Formation from a Calex|4larene Amide that Binds HCl", J.Am. Chem. Soc., vol. 124, No. 10, 2002, pp. 8-19.
Vladimir Sidorov, et al., "Chloride Transport Across Lipid Bilayers and Transmembrane Potential Induction by an Oligophenoxyacetamide", Department of Chemistry and Biochemistry, University of Md., , pp. 20-22.

* cited by examiner

*Primary Examiner*—Shailendra Kumar
(74) *Attorney, Agent, or Firm*—William E. Beaumont; Dickinson Wright, PLLC

(57) ABSTRACT

A compound containing at least two aromatic rings covalently bonded together, with each aromatic ring containing at least one oxyacetamide-based side chain, the compound being capable of forming a chloride ion channel across a lipid bilayer, and transporting chloride ion across the lipid bilayer.

35 Claims, 15 Drawing Sheets

```
                         SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Thr Ala Leu
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Val Ser Tyr Phe
1               5
```

COMPOUNDS HAVING AROMATIC RINGS AND SIDE-CHAIN AMIDE-FUNCTIONALITY AND A METHOD FOR TRANSPORTING MONOVALENT ANIONS ACROSS BIOLOGICAL MEMBRANES USING THE SAME

This application claims benefit of 60/445,160, filed Feb. 5, 2003.

The work leading up to the present invention was supported by the U.S. government, particularly the Department of Energy. As such, the government may have certain rights in the invention pursuant to 35 USC 203.

FIELD OF THE INVENTION

Compounds having aromatic rings and side-chain amide-functionality are provided as well as a method for transporting monovalent anions across biological membranes using the same.

DESCRIPTION OF THE BACKGROUND

Ion transport across cell membranes is essential to living cells. It is well known that certain proteins function as channels in cellular systems for polar and ionic small solutes, such as cations or anions, which are transported across phospholipid bilayers. Ionic Channels of Excitable Membranes, 2nd Edition, Sinauer, Sunderland, Mass. (1992). This conduction is characterized by both ion selectivity and unidirectionality of ion flow.

Ion channels are, in effect, selective pores that allow for the diffusion of ions across cellular membranes. For example, voltage-sensitivity calcium channels mediate the entry of calcium into many types of excitable cells and thus play an important role in neurotransmitter release and excitation-contraction (E-C) coupling. Potassium channels are a group of ubiquitously expressed proteins that serve numerous functions in both excitable and non-excitable cells. See http://rsb.info.nih.gov//Neurochem//BN5ht/MembTransp-BN5.html.

Anion permeability, particularly chloride permeability, is essential for volume, pH and membrane regulation in all cells. Presently, four major families of protein-based chloride channels are known. A growing number of human diseases are known to be caused by mutations in genes encoding these channels. For example, it is known that cystic fibrosis (CF) is caused by mutational defects in a gene encoding protein carriers for chloride channels. See Am J. Resp. Crit. Care Med., Vol. 163, No. 7, June 2001, 1683-1962. See also http://agreem.atsjournals.org/cgi/content/full/163/7/1683.

CF is a common and lethal autosomal recessive genetic disease caused by dysfunction of the cystic fibrosis transmembrane conductance regulator (CFTR) membrane. In fact, absent or defective CFTR function alters both $Na^+$ and $Cl^-$ transport across multiple epithelia, which contributes to both the morbidity and mortality of the disease. Since discover of the ctfr gene more that 800 disease-causing alleles have been identified. See Am J. Resp. Crit. Care Med., id.

The genetics of CF are similar to that of other autosomal recessive diseases in that premature stop mutations within the gene are relatively common. Mutations within this class cause defective CFTR expression which is characterized by reduced mRNA levels, and production of little or no truncated CFTR protein. However, not all of the disease-causing alleles certain premature stop codon mutation.

Efforts have been made to suppress premature stop mutations in the ctfr gene based on the use of certain antibiotics in the aminoglycoside family, such as gentamicin, which function to suppress expression of the mutation stop codon. While the available evidence suggests that gentamicin administration can improve CFTR production and function in cells from patients having premature stop mutations, gentamicin is toxic with long term use. See http://www.personal.umich.edu/~vplec/Gent/gent.html.

This toxicity is unfortunate as long-term therapy is required for CF patients who exhibit the following symptoms: 1) a salt imbalance resulting in secretions of abnormally thick, dehydrated mucous, 2) obstruction of digestive organs, particularly the pancreas, resulting in malnutrition, 3) clogging of lung airways with mucous, rendering them highly susceptible to bacterial infections, and 4) death from lung disease or heart failure before 30 years in about 50% of patients. See Chromosome Aberrations and Associated Diseases, http://www.urnary.edu/~mbusch/NUR319/NUR319Chapter2notes/html.

In view of symptoms 1)-3) noted above, other palliative treatments for CF are also known. For example, deoxyribonuclease has been used to cleave DNA in sputum in order to reduce viscosity. Also, pancreatic enzymes have been administered in order to release protease, amylase and lipase into the digestive tract to compensate for the blocked ducts and tubules of the pancreas. These supplemental enzymes assist in the digestion of carbohydrates and fats which would otherwise be indigestible.

Symptom 3) leads to a host of complications ranging from bacterial infections, asthma, hemotypsis, liver dysfunction, hypoglycemia, gall bladder and kidney stones.

While all of these treatments provide some relief, the mortality rate from CF remains high over time, and, the use of aminoglycosides as stop mutation suppressors or repressors is hampered by long term toxicity. Moreover, as already noted, not all of the disease-causing alleles contain premature stop codon mutations.

Further, while gene therapies have been proposed for treating CF, this approach has not been successful as any positive results obtained are of short duration. This is largely due to the natural defenses of the lung, which defined lung tissue surfaces against allergies including dust particles, bacteria and viruses. This defense system is also effective against viral vectors used to deliver the exogenous, therapeutic genes into cells.

In view of all of these existing therapeutical shortcomings, a need exists for a new approach to transporting chloride ions, across cell membranes, whereby use of toxic repressors for the ctfr gene as well as unreliable gene therapies might be avoided, and which may be used compatibility in conjunction with other existing CF therapies to provide a single comprehensive treatment for CF.

SUMMARY OF THE INVENTION

Accordingly, it is an object of the present invention to provide synthetic compounds which may be used as monovalent anion transporters across biological membranes.

It is also an object of the present invention to provide a method of transporting monovalent anions across biological membranes.

Moreover, it is yet another object of the present invention to provide a method of treating a disease caused by defective expression of chloride-channeling proteins and other diseases characterized by defective anion transport across cell membranes.

It is a further object of the present invention to provide a method for treating cystic fibrosis.

Accordingly, the above objects and others, which will be readily apparent in view of the following description, are provided by a compound containing at least two core aromatic rings which are covalently bonded together, each aromatic ring containing at least one oxyacetamide-based side chain; the compound being capable of forming a monovalent anion channel across a lipid bilayer, and transporting monovalent anion across the lipid bilayer.

DETAILED DESCRIPTION OF THE PREFERRED EMBODIMENTS

Figure 1B:
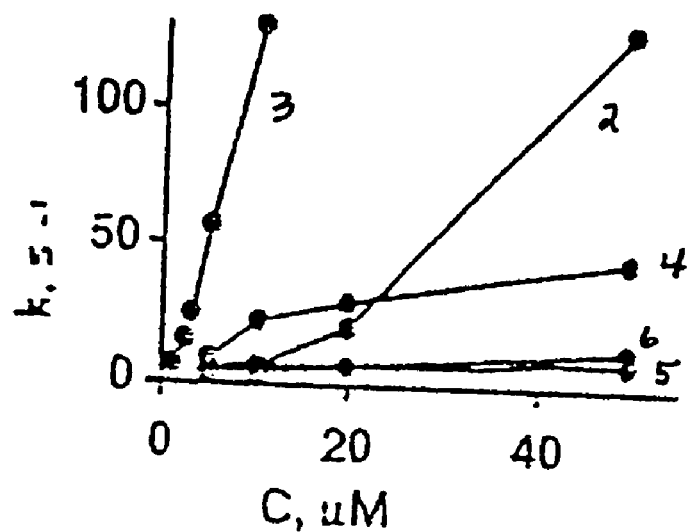
FIGS. 1A and 1B are derived from of pH-stat fluorescent assays with oligophenoxyacetamide compounds 1-6 described herein. Suspensions of EYPC LUVs containing the pH sensitive dye pyranine (ex 405 nm and 460 nm em 510 nm) in a phosphate buffer were used (0.5 mM of lipid, 10 mM $Na_nH_{3-n}PO_4$ n=1, 2, pH 6.4 100 mM NaCl inside and outside) (A) illustrates initial pseudo-first order rate constants in the presence of 5 μm of ionophores 1-6 (1 mol % injection of 20 μl of 0.5 mM DMSO solution of 1-6 into 1.9 mL of vesicular suspension was followed by injection of 21 μl of 0.5 M NaOH and final lysis of liposomes with Triton X-100; (B) illustrates initial pseudo-first order rate constants assessed for various concentrations of oligomeric ionophores 2-6. The same experimental protocol as in (A) was used. Legend for traces denotes use of oligocompounds 2, 3, 4, 5, 6.

The present invention is based, in part, on the discovery of a new class of synthetic compounds that form anion ion channels across lipid bilayers, and which transport chloride ions across bilayers.

Generally, the compounds of the present invention contain at least two core aromatic rings bonded together, with each ring containing at least one oxyacetamide-based side chain, the compound being able to form monovalent anion channels is a lipid bilayer, and being able to transport the anion through the bilayer.

As used herein, the term core "aromatic" ring "means any aromatic ring of 5 or 6 ring atoms, which may include at least one heterocyclic atom, such as nitrogen. For example, aromatic rings, such as phenyl, pyrrolyl or pyridyl may be mentioned. These rings may be used in combination or exclusively. Moreover, the core aromatic rings are generally covalently bonded together, but are not fused together.

Further, the core aromatic rings are generally covalently bonded together by a methylene group, and the aromatic rings may form a linear oligomeric structure, or they may be joined together to form a macrocyclic structure, such as a calixarene structure. Calixarenes are well known, as are synthetic procedures for producing the same.

For example, the compounds may have the formula (I):

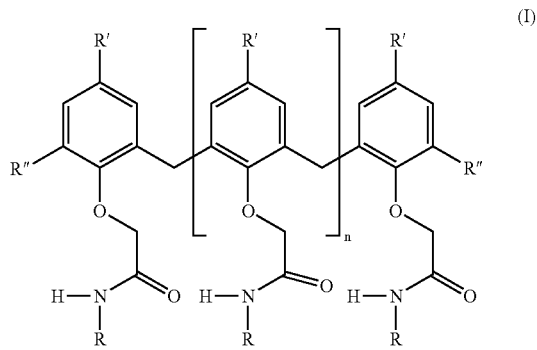

wherein:

n is 0 up to about 12.

R is acyclic or cyclic alkyl of 1 to 12 carbons, aromatic, heterocyclic or peptide groups;

R' and R" are each independently —H, acyclic or cyclic alkyl of 1 to 12 carbons, aromatic, heterocyclic or peptide groups; and R is —H, acyclic or cyclic alkyl of 1 to 12 carbons, aromatic, heterocyclic or peptide groups.

As used herein, the term "alkyl" means $C_1$—$C_{18}$ alkyl, which may be cyclic or acyclic linear or branched $C_1$—$C_{18}$ alkyl, which are preferably branched $C_1$—$C_{18}$ alkyl. Groups such as methyl, ethyl, n-propyl, i-propyl, n-butyl, sec-butyl, tert-butyl, n-pentyl, n-hexyl, n-heptyl, n-oxtyl, n-nonyl, n-decyl, n-undecyl, and dodecyl may be mentioned as examples of acyclic alkyl group. Groups such as n-cyclopentyl, n-cyclohexyl, and n-cycloheptyl may be mentioned as examples of cyclic alkyl groups. The "alkyl" groups may be substituted by methyl, ethyl, methoxy, ethoxy, nitro, hydroxyl or halo, for example.

As used herein, the term "aromatic" for R', R' or R" or non-core aromatic means phenyl or benzyl, for example, which may be substituted by one or more lower alkyl or alkoxy groups, as well as halo, nitro or hydroxyl, for example.

As used herein, the term "heterocyclic" means imidazolyl, pyridyl, pyrrolyl or furanyl, for example, each of which may be substituted by lower alkyl, lower alkoxy, halo, nitro or hydroxyl, for example.

As used herein, the term "peptide" means an amino acid sequence of from only one amino acid sequence of from only one amino acid unit to up to about 10 amino acids. This "peptide" may contain any of the known amino acids in any sequence. It is preferred that the peptide be from 1-6 amino acid units, more preferably from 1-3.

Any of known amino acids may be used in any sequential combination. For example sequences such as Ala-Phe-Ile, Ser-Thr-Ala-Leu (SEQ ID NO: 1) or Ala-Val-Ser-Tyr-Phe (SEQ ID NO: 2) may be used.

While R, R', and R" may be as defined above, of particular interest are compounds where at least one of R or R is —H. It is of more particular interest where both of R' and R" are —H.

Of particular interest is the compound, where n is 0-3, and R is $C_2$—$C_6$ linear alkyl. Of very particular interest is the compound, wherein n is 1 and R is n-butyl.

As used herein, the term "oligomer" or "oligocompound" is used to describe all compounds not having a macrocycle structure, including the monomer, where n is 1; the dimer, where n is 2; the trimer, where n is 3; the tetramer, where n is 4; the pentamer, where n is 5; and the hexamer, where n is 6, for example.

As noted, the compounds of the present have the ability to transport monovalent anions, such as biocarbonate or chlorine anions, for example, across lipid bilayers, such as cell membranes. It is of particular advantage to use these compounds to transport chloride anions across lipid bilayers.

Generally, the oligomer compounds of the formula (I) may be obtained using well known reactions. For example, these compounds may be obtained by condensing short chain oligomers with formaldehyde under basic conditions to form oligomethylene-p-tert-butylphenols. This is followed by acid-catalyzed chain elongation of the o-hydroxymethylene intermediates with p-tert-butylphenols are then dealkylated. After o-alkylation with ethyl bromoacetate, the esters formed are saponified to give oligophenoxyacetic acids. Activation of the oligophenoxyacetic acids with thioyl chloride, followed by reaction with butylamine, for example affords the secondary amide.

For example, the aromatic rings may include combinations of unsubstituted or substituted phenyl and pyridyl rings, or phenyl and pyrrolyl rings.

The present invention will now be further discussed by reference to the following examples which are provided solely for purposes of illustration and are not intended to be limitative.

Hereinbelow are, in order, 1) examples of synthetic protocols for oligophenoxyacetamide compounds 2-6 is depicted schematically in Scheme "S1", 2) protocols for fluorimetric transport assays, and 3) protocols for $^{35}$Cl NMR transport assays for these compounds.

General. The $^1$H NMR spectra were recorded on a Bruker DRX400 instrument operating at 400.130 MHz. Chemical shifts are reported in ppm relative to the residual protonated solvent peak. The $^{13}$C NMR spectra were recorded on the same instrument at 100.613 MHz and chemical shift values are reported in ppm relative to the solvent peak. Both $^1$H and $^{13}$C spectra were taken in the same solvent for each sample. Mass spectra were recorded on a JEOL SX-102A magnetic sector mass spectrometer using the fast atom bombardment (FAB) technique. All fluorimetric experiments were carried out on an SLM Aminco® (Aminco Bowman® Series 2) Luminescence Spectrometer. Vapor pressure osmometry (VPO) was performed on a Wescor 5520, Vapro™ instrument. The pH of solutions was monitored with an Orion pH-meter, model 420A, with a Ag/AgCl pH-sensitive electrode. Chromatography was performed using 60-200 mesh silica purchased from Baker and 40-120 μ Sephadex G-10 purchased from Pharmacia Fine Chemicals. Thin layer chromatography was performed on Kieselgel 60 F254 and Uniplate™ Silica Gel GF silica-coated glass plates and visualized by UV and $I_2$. High-pressure extrusion was performed on the Avanti™ mini-extruder with a 0.1 μm polycarbonate membrane. All chemicals and solvents were purchased from Sigma, Fluka, Aldrich or Acros. EYPC was purchased from Avanti Polar Lipids.

Synthesis The general synthetic scheme for the compounds 2-6 shown in Scheme S1. The synthesis of calix[4] arene C1, calix[4]arene C2 and N-butyl-2-phenyoxyacetamide 1 was reported previously.

Scheme S1
Synthesis of butylamides 2-6.

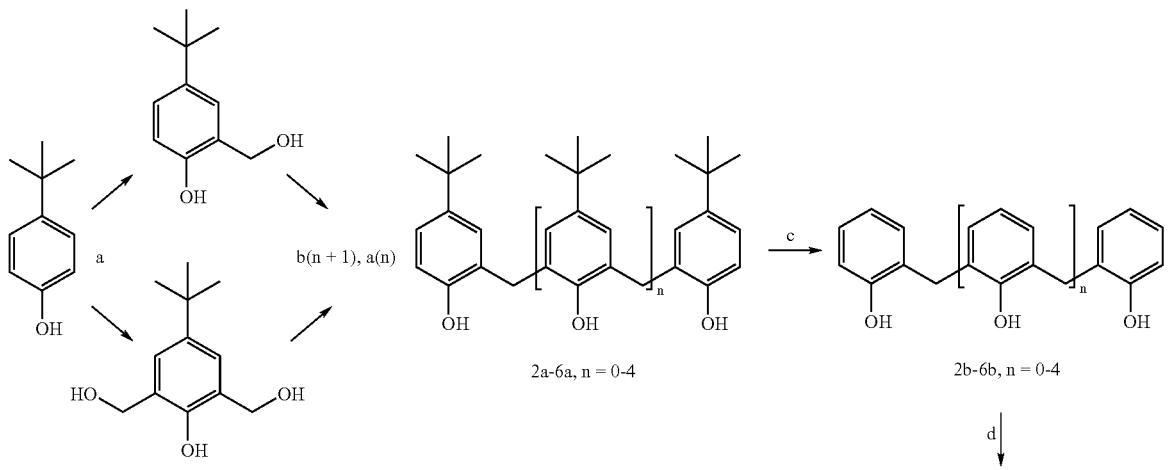

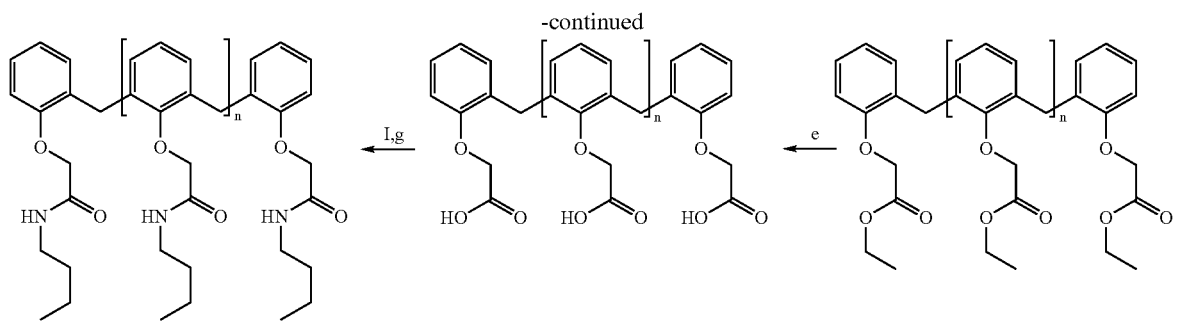

2-6, n = 0-4　　　　　2b-6b, n = 0-4　　　　　2b-6b, n = 0-4 a), b) and c) literature procedures, d) BrCH₂COOEt, acetone, Cs₂CO₃, reflux, e) KOH aq, THF, MeOH, rt, f) SOCl₂, benzene, g) BuNH₂, Et₃N, CH₂Cl₂, rt.

Bis-(ethyl phenoxyacetate) 2c. Diphenol 2b (382 mg, 1.91 mmol), ethyl bromoacetate (0.87 g, 5.2 mmol) and $Cs_2CO_3$ (1.24 g, 3.82 mmol) were suspended in 50 mL of acetone, and stirred under reflux overnight. The reaction mixture was cooled to the room temperature, the solvent evaporated under reduced pressure. The residual solid was partitioned in chloroform-water, and the organic layer washed with 0.1 N HCl. The organic layer was separated and solvent removed under reduced pressure. The crude solid was purified by the column chromatography (silica gel, methylene chloride), and 537 mg of bis-(ethyl phenoxyacetate) 2c was obtained (1.44 mmol, 75%) $^1$H NMR (DMSO-d6, 25° C.) δ: 715-7.10 (m, 4 H, Ar—H), 6.86-6.83 (m, 4 H, Ar—H), 4.78 (s, 4 H, Ar—O—CH₂—CO), 4.17 (q, 4 H, J=7.1 Hz, Ar—O—CH₂—CO—CH₂—CH₃), 3.96 (s, 2 H, Ar—CH₂—Ar), 1.21 (t, 6 H, J=7.1 Hz, Ar—O—CH₂—CO—CH₂—CH₃). $^{13}$C δ: 169.3, 155.9, 130.8, 129.1, 127.6, 121.4, 112.0, 65.4, 61.0, 29.6, 14.5. MS (FAB) ([M+H]⁺):373.1, calcd for $C_{21}H_{24}O_6$ 372.16.

Diphenoxyacetic acid 2d. Bis-(ethyl phenoxyacetate) 2c (476 mg, 1.28 mmol) was dissolved in 3 mL MeOH and 5 mL THF, and 1 mL of 45% aqueous KOH was added dropwise. The reaction mixture was stirred overnight at room temperature under nitrogen, evaporated to dryness, dissolved in 10 mL of water and acidified with 6 N HCl to pH 1. The precipitate formed was filtered and washed with water. The aqueous layer was extracted with chloroform 4 times, the organic layer separated and solvent removed under reduced pressure. The solid formed was recombined with the filtrate and dried for 3 hrs under high vacuum to give 434 mg of diphenoxyacetic acid 2d (1.37 mmol, 107%). $^1$H NMR (DMSO-d6, 25° C.) δ: 7.12-7.06 (m, 4 H, Ar—H), 6.82-6.78 (m, 4 H, Ar—H), 4.56 (s, 4 H, Ar—O—CH₂—CO), 3.95 (s, 2 H, Ar—CH₂—Ar). $^{13}$C δ: 170.8, 156.4, 130.7,129.2, 127.4, 120.9, 112.1, 66.1, 29.5. MS (FAB) ([M+H]³⁰): 317.1, calcd for $C_{17}H_{16}O_6$ 316.09.

Bis-(N-butyl-2-phenyoxyacetamide) 2. Diphenoxyacetic acid 2d (418 mg, 1.32 mmol) was suspended in benzene (25 mL), and SOCl₂ (2 mL, 27.4 mmol) was added. The reaction mixture was stirred under reflux for 2.5 hours. Over the course of the reaction, the turbid suspension changed into a yellow transparent solution. The reaction mixture was cooled to room temperature, the solvent and excess of thionyl chloride was removed under reduced pressure, and the remaining traces of thionyl chloride were removed by subsequent co-evaporation with benzene. Diphenoxyacetyl chloride was reacted without further purification. The total amount obtained was dissolved in 25 mL of dry CH₂Cl₂ and Et₃N (556 μL, 3.99 mmol) and BuNH₂ (652 μL, 6.6 mmol) were added. The reaction mixture was stirred overnight at room temperature, the solvent was evaporated under reduced pressure, and the resulting oil was dried under high vacuum, dissolved in chloroform and washed with water. The organic layer was separated, dried over sodium sulfate, and the solvent removed under reduced pressure. Purification by column chromatography (silica gel, MeOH:CH₂Cl₂ 1:99) gave 448 mg of bis-(N-butyl-2-phenoxyacetamide) 2 (1.05 mmol, 85% from 2c). $^1$H NMR (DMSO-d6, 25° C.) δ: 7.62 (t, 2H, J=6 Hz, CONH), 7.16 (dt, 2 H, J=1.6 Hz, 7.8 Hz, Ar—H), 7.03 (dd, 2 H, J=1.2 Hz, 7.6 Hz, Ar—H), 6.90-6.85 (m, 4 H, Ar—H), 4.45 (s, 4 H, Ar—O—CH₂—CO), 4.04 (s, 2 H, Ar—CH₂—Ar), 3.08 (app q, 4 H, J=6.8 Hz, NH—CH₂—CH₂—CH₂—CH₃), 1.35 (m, 4 H, J=7.2 Hz, NH—CH₂—CH₂—CH₂—CH₂—CH₃), 1.21 (m, 4 H, J=7.2 Hz, NH—CH₂—CH₂—CH₂—CH₃), 0.83 (t, 6 H, J=7.2 Hz, NH—CH₂—CH₂—CH₂—CH₃). $^{13}$C δ: 167.8, 156.0, 130.6, 129.2, 127.7, 121.5, 112.3, 67.7, 38.4, 31.6, 30.0, 19.9, 14.1. MS (FAB) ([M+H]⁺): 427.31, calcd for $C_{25}H_{34}N_2O_4$ 426.25.

Tris-(ethyl phenoxyacetate) 3C. Triphenol 3b (53 mg, 0.17 mmol), ethyl bromoacetate (117 mg, 0.70 mmol) and Cs₂CO₃ (166 mg, 0.51 mmol) were suspended in 25 mL of acetone, and stirred under reflux overnight. The reaction mixture was cooled to room temperature, the solvent evaporated under reduced pressure, the residual solid was suspended in chloroform-water, and the organic layer washed with 0.1 N HCl. The organic layer was separated and solvent removed under reduced pressure. The crude solid was purified by column chromatography (silica gel, methylene chloride), and 68 mg of tris-(ethyl phenoxyacetate) 3c was obtained (0.14 mmol, 83%). $^1$H NMR (CDCl₃, 25° C.) δ: 7.15-6.72 (m, 11 H, Ar—H), 4.60 (s, 4 H, Ar—O-CH₂—CO), 4.39 (s, 2 H, Ar—O—CH₂—CO), 4.25-4.18 (m, 6 H, Ar—O—CH₂—CO—CH₂—CH₃), 4.12 (s, 4 H, Ar—CH₂—Ar), 1.25 (ap t, 9 H, J=7.2 Hz, Ar—O—CH₂—CO—CH₂—CH₃). $^{13}$C δ: 169.1, 169.0, 155.9, 155.0, 133.6, 131.0, 129.7, 129.0, 127.3, 124.5, 121.6, 111.4, 70.1, 65.7, 61.2, 61.0, 29.7, 14.1. MS (FAB) ([M+H]⁺); 565.19, calcd for $C_{32}H_{36}O_9$ 564.24.

Triphenoxyacetic acid 3d. Tris-(ethyl phenoxyacetate) 3c (59 mg, 0.104 mmol) was dissolved in 2 mL MeOH and 2 mL THF, and 0.7 mL of 45% aqueous KOH was added dropwise. The reaction mixture was stirred overnight at room temperature under nitrogen, evaporated to dryness, dissolved in 2 mL of water, acidified with 6 N HCl to pH 1, and the precipitate formed was filtered and washed with water. The aqueous layer was extracted with chloroform 4 times, the organic layer separated and solvent removed under reduced pressure. The solid formed was recombined with the filtrate and dried for 6 hrs under high vacuum to give 57 mg of triphenoxyacetic acid 3c. $^1$H NMR (acetone-d6, 25° C.) δ: 7.2-6.85 (m, 1 H, Ar—H), 4.70 (s, 4 H, Ar—O—CH$_2$—CO), 4.49 (s, 2 H, Ar—O—CH$_2$—CO), 4.13 (s, 4 H, Ar—CH$_2$—Ar). $^{13}$C δ: 170.4, 156.8, 155.8, 134.7, 131.5, 130.4, 129.7, 128.1, 125.1, 122.0, 117.7, 112.5, 70.4, 65.6, 30.1

Tris-(N-butyl-2-phenoxyacetamide) 3. Triphenoxyacetic acid 3d (48 mg, 0.1 mmol) was activated with SOCl$_2$ (1 mL in 3 mL of benzene, 13.7 mmol) by the same procedure as described for the compound 3. The triphenoxyacetyl chloride was reacted without purification. The total amount obtained was dissolved in 10 mL of dry CH$_2$Cl$_2$, and Et$_3$N (125 μL, 0.9 mmol, 3-fold excess) and BuNH$_2$ (150 μL, 1.5 mmol, 5-fold excess) were added. The reaction mixture was stirred overnight at room temperature, the solvent was evaporated under reduced pressure, and the resulting oil was dried under high vacuum, dissolved in chloroform and washed with water. The organic layer was separated, and solvent removed under reduced pressure. Purification by column chromatography (silica gel, MeOH:CH$_2$Cl$_2$ 2:98) gave 51 mg of tris-(N-butyl-2-phenoxyacetamide) 3 (0.079 mmol, 89% from 3c) as white crystals. $^1$H NMR (DMSO-d6, 25° C.) δ: 7.99 t, 1 H, J=5.6 Hz, CONH), 7.66 t, 2 H, J=5.6 Hz, CONH), 7.18 (dt, 2 H, J=1.6 Hz, 8 Hz, Ar—H), 7.04 (dd, 2 H, J=1.6 Hz, 8 Hz, Ar—H), 6.96-6.87 (m, 7 H, Ar—H), 4.43 (s, 4 H, Ar—O—CH$_2$—CO), 4.19 (s, 2 H, Ar—O—CH$_2$—CO), 4.06 (s, 4 H, Ar—CH$_2$—Ar), 3.13-3.05 (m, 6 H, NH—CH$_2$—CH$_2$—CH$_2$—CH$_3$), 1.43-1.31 (m, 6 H, NH—CH$_2$—CH$_2$—CH$_2$—CH$_3$), 1.28-1.16 (m, 6 H, NH—CH$_2$—CH$_2$—CH$_2$—CH$_3$), 0.82 (t, 9 H, J=7.6 Hz, NH—CH$_2$—CH$_2$—CH$_2$—CH$_3$). $^{13}$C δ: 167.3, 155.4, 154.4, 133.4, 130.3, 128.8, 128.5, 127.5, 124.3, 121.0, 111.8, 38.0, 31.2, 29.3, 19.5, 13.6; MS (FAB) ([M+H]$^+$): 646.42, calcd for C$_{38}$H$_{51}$N$_3$O$_6$ 645.38.

Tetrakis-(ethyl phenoxyacetate) 4c. Tetraphenol 4b (571 mg, 1.38 mmol), ethyl bromoacetate (1.38 g, 8.3 mmol) and Cs$_2$CO$_3$ (1.8 g, 5.5 mmol) were suspended in 25 mL of acetone, and stirred under reflux overnight. The reaction mixture was cooled down to the room temperature, the solvent evaporated under reduced pressure, the residual solid was partitioned in chloroform-water, and the organic layer washed with 0.1 N HCl. The organic layer was separated and solvent removed under reduced pressure. The crude solid was purified by the column chromatography (silica gel, ethyl acetate:hexanes 1:2), and 800 mg of the tetrakis-(ethyl phenoxyacetate) 4c was obtained (1.06 mmol, 76.6%). $^1$H NMR (DMSO-d6, 25° C.) δ: 7.16 (dt, 2 H, J=1.6 Hz, 8.0 Hz, Ar—H), 7.06 (dd, 2 H, J=1.6 Hz, 8.0 Hz, Ar—H), 6.97-6.83 (m, 10 H, Ar—H), 4.77 (s, 4 H, Ar—O—CH$_2$—CO), 4.43 (s, 4 H, Ar—O—CH$_2$—CO), 4.17-4.08 (m, 8 H, Ar—O—CH$_2$—CO—CH$_2$—CH$_3$), 4.05 (s, 2 H, Ar—CH$_2$—Ar), 4.00 (s, 4 H, Ar—CH$_2$—Ar), 1.20 -1.14 (m, 12 H, Ar—O—CH$_2$—CO—CH$_2$—CH$_3$), $^{13}$C δ: 169.2, 169.0, 155.8, 155.1, 134.0, 130.9, 129.2, 129.0, 127.9, 124.4, 121.5, 112.2, 70.1, 65.3, 61.0, 61.0, 29.5, 14.4, 14.4. MS (FAB) (([M+H]$^+$): 757.18, calcd for C$_{43}$H$_{48}$O$_{12}$ 756.31.

Tetraphenoxyacetic acid 4d. Tetrakis-(ethyl phenoxyacetate) 4c (765 mg, 1.01 mmol) was dissolved in 3 mL MeOH and 3 mL THF, and 1 mL of 45% aqueous KOH was added dropwise. The reaction mixture was stirred overnight at room temperature under nitrogen, evaporated to dryness, dissolved in 10 mL of water, acidified with 6 N HCl to pH 1, the precipitate formed was filtered and washed with water. The aqueous layer was extracted with chloroform 4 times, the organic layer separated and solvent removed under reduced pressure. The solid formed was recombined wit the filtrate and dried for 4 hrs under high vacuum to give 677 mg of tetraphenoxyacetic acid 4d. $^1$H NMR (DMSO-d6, 25° C.) δ: 13.80 (s, 4 H, COOH), 7.55 (dt, 2 H, J=1.6 Hz, 7.8 Hz, Ar—H), 7.44 (dd, J=1.6 Hz, 7.8 Hz, Ar—H), 7.32-7.17 (m, 10 H, Ar—H), 4.86 (s, 4 H, Ar—O—CH$_2$—CO), 4.51 (s, 4 H, Ar—O—CH$_2$—CO), 4.20 (s, 2 H, Ar—CH$_2$—Ar), 4.13 (s, 4 H, Ar—CH$_2$—Ar), $^{13}$C δ: 170.3, 170.1, 155.6, 154.8, 133.6, 130.4, 128.8, 128.6, 127.4, 124.4, 120.9, 111.7, 69.7, 64.8, 29.1, 29.0. (FAB) ([M+H]$^+$): 645.03, calcd for C$_{35}$H$_{32}$O$_{12}$ 644.19.

Tetrakis-(N-butyl-2-phenoxyacetamide) 4. Tetraphenoxyacetic acid 4d (649 mg, 1.05 mmol) was activated with SOCl$_2$ (5 mL in 15 mL of benzene, 68.5 mmol) by the same procedure as described for the compound 2. The tetraphenoxyacetyl chloride was reacted without purification. The total amount obtained was dissolved in 25 mL of dry CH$_2$Cl$_2$ and 3.4 mL of Et$_3$N (24.4 mmol, 6-fold excess) and 4.1 mL of BuNH$_2$ (41.4 mmol, 10-fold excess) were added subsequently. The reaction mixture was stirred overnight at room temperature, the solvent was evaporated to dryness under reduced pressure, and the resulting oil was dried under high vacuum, dissolved in chloroform and washed with water. The organic layer was separated, and solvent removed under vacuum. Purification by column chromatography (silica gel, MeOH:CH$_2$Cl$_2$ 2.98 vv) gave 577 mg of tetrakis-(N-butyl-2-phenoxyacetamide) 4 (0.67 mmol, 66% from 4c). $^1$H NMR (DMSO-d6, 25° C.) δ: 7.98 (t, 2 H, J=5.8 Hz, CO—NH), 7.68 (t, 2 H, J=5.8 Hz, CO—NH), 7.18 (dt, 2 H, J=1.2 Hz, 7.6 Hz, Ar—H), 7.03 (dd, 2 H, J=1.2 Hz, 7.6 Hz, Ar—H), 6.98-6.84 (m, 10 H, Ar—H), 4.43 (s, 4 H, Ar—O—CH$_2$—CO), 4.14 (s, 4 H, Ar—O—CH$_2$—CO), 4.08 (s, 2 H, Ar—CH$_2$—Ar), 4.05 (s, 4 H, Ar—CH$_2$—Ar), 312-3.05 (m, 8 H, NH—CH$_2$—CH$_2$—CH$_2$—CH$_3$), 1.39-1.33 (m, 8 H, NH—CH$_2$—CH$_2$—CH$_2$—CH$_3$), 1.25-1.17 (m, 8 H, NH—CH$_2$—CH$_2$—CH$_2$—CH$_3$), 0.82 (t, 12 H, J=7.4 Hz, NH—CH$_2$—CH$_2$—CH$_2$—CH$_3$). $^{13}$C δ: 167.3, 155.4, 154.4, 133.5, 133.4, 130.2, 128.7, 127.5, 124.4, 121.1, 111.8, 71.8, 67.1, 37.9, 31.2, 31.1, 29.3, 19.5, 19.5, 13.6. (FAB) ([M+H]$^+$): 865.4, calcd for C$_{51}$H$_{68}$N$_4$O$_8$ 864.51.

Pentakis-(ethyl phenoxyacetate) 5c. Pentaphenol 5b (508 mg, 0.98 mmol), ethyl bromoacetate (1.23 g, 7.4 mmol, 1.5-fold excess) and Cs$_2$CO$_3$ (1.6 g, 4.9 mmol) were suspended in 25 mL of acetone, and stirred under reflux overnight. The reaction mixture was cooled down to the room temperature, the solvent evaporated under vacuum, the residual solid was partitioned in chloroform-water, and the organic layer washed with 0.1 N HCl. The organic layer was separated and solvent removed under vacuum. The crude solid was submitted to the column chromatography (silica gel, ethyl acetate:hexanes 1:2), and 540 mg of the product was obtained (0.57 mmol, 58%). $^1$H NMR (DMSO-d6, 25° C.) 7.16 (dt, 2 H, j1=1.6 Hz, j2=7.8 Hz, Ar—H), 7.06 (dd, j1=1.6 Hz, j2=7.6 Hz, Ar—H), 7.00-6.82 ( m, 13 H, Ar—H), 4.77 (s, 4 H, Ar—O—CH$_2$—CO), 4.43 (s, 4 H, Ar—O—CH$_2$—CO), 4.40 (s, 2 H, Ar—O—CH$_2$—CO), 417-4.08 (m, 10 H, Ar—O—CH$_2$—CO—CH$_2$—CH$_3$), 4.06 (s, 4 H, Ar—CH$_2$—Ar), 4.01 (s, 4 H, Ar—CH$_2$—Ar), 1.20-1.13 (m, 15 H, Ar—O—CH$_2$—CO—CH$_2$—CH$_3$), $^{13}$C δ: 169.2, 169.0, 155.8, 155.3, 155.1, 134.0, 134.0, 133.9, 130.9, 129.2, 129.0, 127.9, 125.0, 124.9, 121.5, 112.2, 70.1, 65.3, 61.0, 61.0, 29.7, 29.5, 14.4, 14.4. (FAB) ([M+H]$^+$): 949.1, calcd for C$_{54}$H$_{60}$O$_{15}$ 948.39.

Pentaphenoxyacetic acid 5d. Pentakis-(ethyl phenoxyacetate) (515 mg, 0.54 mmol) was dissolved in 3 mL MeOH and 2 mL THF, and 1 mL of 45% aqueous KOH was added dropwise. The reaction mixture was stirred overnight at room temperature under nitrogen, co-evaporated with acetone to dryness, acidified with 6 N HCl to pH 1, and co-evaporated with acetone to dryness. The solid residue was triturated with acetone, the precipitate filtered out, and the organic solution was evaporated to dryness to give 509 mg of the product. $^1$H NMR (DMSO-d6, 25° C.) δ: 12.92 (s, 5 H, COOH), 7.16 (dt, j1=Hz, j2=Hz, Ar—H), 7.07 (dd, 2 H, j1=Hz, j2=Hz, Ar—H), 6.96-6.80 (m, 13 H, Ar—H), 4.67 (s, 4 H, Ar—O—CH$_2$—CO), 4.36 (s, 4 H, Ar—O—CH$_2$—CH$_2$—CO), 4.34 (s, 2 H, Ar—O—CH$_2$—CO), 4.08 (s, 4 H, Ar—CH$_2$—Ar), 4.01 (s, 4 H, Ar—CH$_2$—Ar). $^{13}$C δ: (FAB) ([M+H]$^+$) : 809.0, calcd for C$_{44}$H$_{40}$O$_{15}$ 808.2

Pentakis-(N-butyl-2-phenoxyacetamide) 5. Pentaphenoxyacetic acid (515 mg, 0.64 mmol) was activated with SOCl$_2$ (3 mL in 10 mL of dry benzene, 41.1 mmol, 13-fold excess.) by the same procedure as described for the compound 3. The pentaphenoxyacetyl chloride was reacted without purification. The total amount obtained was dissolved in 25 mL of dry CH$_2$Cl$_2$ and 3 mL of Et$_3$N (21.5 mmol, 6.7-fold excess) and 3 mL of BuNH$_2$ (30.3 mmol, 9.5-fold excess) were added subsequently. The reaction mixture was stirred overnight at room temperature, the solvent was evaporated to dryness under reduced pressure, and the resulting oil was dried under high vacuum, dissolved in chloroform and washed with water. The organic layer was separated, and solvent removed under vacuum. Purification by column chromatography (silica gel, MeOH:CH$_2$Cl$_2$ 3:97) gave 480 mg (0.44 mmol, 80%, from5c) of pentakis-(N-butyl-2-phenoxyacetamide) 5. $^1$H NMR (DMSO-d6, 25° C.) δ: 7.97-7.95 (m, 3 H, CO—NH), 7.66 (t, 2 H, j=5.6 Hz, CO—NH), 7.18 (app t, 2 H, J=7.8 Hz, Ar—H), 7.03 (app d, 2 H, J=7.2 Hz, Ar—H), 6.99-6.84 (m, 13 H, Ar—H), 4.43 (s, 4 H, Ar—O—CH$_2$CO), 4.14 (s, 4 H, Ar—O—CH$_2$—CO), 4.11 (s, 2 H, Ar—O—CH$_2$—CO), 4.08 (s, 4 H, Ar—CH$_2$—CO), 4.05 (s, 4 H, Ar—CH$_2$—Ar), 3.12-3.05 (m, 10 H, NH—CH$_2$—CH$_2$—CH$_2$—CH$_3$), 1.41-1.31 (m, 10 H, NH—CH$_2$—CH$_2$—CH$_2$—CH$_3$), 1.27-1.17 (m, 10 H, NH—CH$_2$—CH$_2$—CH$_2$—CH$_2$—CH$_3$), 0.83-0.80 (m, 15 H, NH—CH$_2$—CH$_2$—CH$_2$—CH$_3$). $^{13}$C δ: 167.8, 167.8, 167.7, 155.9, 154.9, 154.8, 134.0, 133.9, 133.9, 130.7, 129.3, 129.2, 129.2, 129.0, 129.0, 128.0, 124.9, 121.5, 112.3, 72.2, 72.1, 67.6, 31.6, 31.6, 29.7, 29.5, 19.9, 19.9, 14.1. (FAB) ([M+H]$^+$): 1084.30, calcd for C$_{64}$H$_{85}$N$_5$O$_{10}$ 1083.63.

Hexakis-(ethyl phenoxyacetate) 6c. Hexaphenol 6b (253 mg, 0.41 mmol), ethyl bromoacetate (0.616 g, 3.7 mmol) and Cs$_2$CO$_3$ (0.802 g, 2.5 mmol) were suspended in 40 mL of acetone, and stirred under reflux overnight. The reaction mixture was cooled to room temperature, the solvent evaporated under reduced pressure, the residual solid was partitioned in chloroform-water, and the organic layer washed with 0.1 N HCl. The organic layer was separated and solvent removed under reduced pressure. The crude solid was submitted to the column chromatography (silica gel, ethyl acetate:hexanes 1:2), and 211 mg of the hexakis-(ethyl phenoxyacetate) 6c was obtained (0.19 mmol, 46%). $^1$H NMR (CDCl$_3$, 25° C.) 7.15 (dt, 2 H, J=1.6 Hz, 7.9 Hz, Ar—H), 7.08 (dd, 2 H, J=1.6 Hz, 7.2 Hz, Ar—H), 6.98-6.84 (m, 16 H, Ar—H), 4.6 (s, 4 H, Ar—O—CH$_2$—CO), 4.37 (s, 4 H, Ar—O—CH$_2$—CO), 4.34 (s, 4 H, Ar—O—CH$_2$—CO), 4.24-4.07 (m, 22 H, Ar—O—CH$_2$—CO—CH$_2$—CH$_3$ and Ar—CH$_2$—Ar), 1.27-1.13 (m, 18 H, Ar—O—CH$_2$—CO—CH$_2$—CH$_3$). $^{13}$C δ: (FAB) ([M+Na]$^+$): 1163.04, called for C$_{65}$H$_{72}$O$_{18}$ 1140.47.

Hexaphenoxyacetic acid 6d. Hexakis-(ethyl phenoxyacetate) 6c (202 mg, 0.18 mmol) was dissolved in 1 mL MeOH and 2 mL THF, and 0.3 mL of 45% aqueous KOH was added dropwise. The reaction mixture was stirred overnight at room temperature under nitrogen, co-evaporated with acetone to dryness, acidified with 6 N HCl to pH 1, and co-evaporated with acetone. The solid residue was triturated with acetone, the precipitate filtered out, and the organic solution was evaporated under reduced pressure and dried under high vacuum to give 201 mg of the product. $^1$H NMR (DMSO-d6, 25° C.) δ: 12.86 (s, 6 H, COOH), 7.13 (dt, J=1.6 Hz, 7.9 Hz, Ar—H), 7.03 (dd, 2 H, J=1.6 Hz, 7.2 Hz, Ar—H), 6.96-6.79 (m, 16 H, Ar—H), 4.65 (s, 4 H, Ar—O—CH$_2$—CO), 4.33 (s, 4 H, Ar—O—CH$_2$—CO), 4.32 (s, 4 H, Ar—O—CH$_2$—CO), 4.06 (br s, 6 H, Ar—CH$_2$—Ar), 3.98 (s, 4 H, Ar—CH$_2$—Ar).

Hexakis-(N-butyl-2-phenoxyacetamide) 6. Hexaphenoxyacetic acid 7d (201 mg, 0.20 mmol) was activated with SOCl$_2$ (1.9 mL in 10 mL of dry benzene, 26.0 mmol) by the same procedure as described for the compound 3. The hexaphenoxyacetyl chloride was reacted without purification. The total amount obtained was dissolved in 10 mL of dry CH$_2$Cl$_2$ and Et$_3$N (0.5 mL, 3.6 mmol) and BuNH$_2$ (0.5 mL, 5.5 mmol) were added. The reaction mixture was stirred overnight at room temperature, the solvent was evaporated under reduced pressure, and the resulting oil was dried under high vacuum, dissolved in chloroform and washed with water. The organic layer was separated, and solvent removed under pressure. Purification by column chromatography (silica gel, MeOH:CH$_2$Cl$_2$ 3.97) gave 160 mg (0.12 mmol, 68% from 6c) of hexakis-(N-butyl-2-phenoxyacetamide) phenoxyacetamide) 6. $^1$H NMR (DMSO-d6, 25° C.) δ: 7.97-7.93 (m, 4 H, CO—NH), 7.65 (t, 2 H, J=6.0 Hz, CO—NH), 7.16 (dt, 2 H, J=1.6 Hz, 7.9 Hz, Ar—H), 7.03 (dd, 2 H, J=1.6 Hz, 7.2 Hz, Ar—H), 7.00-6.84 (m, 16 H, Ar—H), 4.43 (s, 4 H, Ar—O—CH$_2$—CO), 4.13 (s, 4 H, Ar—O—CH$_2$—CO), 4.10 (s, 4 H, Ar—O—CH$_2$—CO), 4.07 (s, 6 H, Ar—CH$_2$—Ar), 4.04 (s, 4 H, Ar—CH$_2$-Ar), 3.12-3.04 (m, 12 H, NH—CH$_2$—CH$_2$—CH$_2$—CH$_3$), 1.41-1.31 (m, 12 H, NH—CH$_2$—CH$_2$—CH$_2$—CH$_3$), 1.27-1.17 (m, 12 H, NH—CH$_2$—CH$_2$—CH$_2$—CH$_2$—CH$_3$), 0.83-0.79 (m, 18 H, NH—CH$_2$—CH$_2$—CH$_2$—CH$_3$), $^{13}$Cδ: 167.3, 167.2, 155.4, 154.4, 133.5, 133.4, 130.2, 128.8, 128.7, 128.6, 127.5, 124.5, 124.4, 121.0, 111.8, 71.8, 71.7, 67.1, 37.9, 31.1, 29.3, 29.1, 19.5, 19.4, 13.6. (FAB) ([M+H]$^+$): 1303.37, calcd for C$_{77}$H$_{102}$N$_6$O$_{12}$ Cs 1302.76.

Fluorimetric Transport Assays

Liposome Preparation for Fluorimetric Assays. Egg yolk L-α-phosphatidylcholine (EYPC ethanol solution, 60 μL, 79 μmol) was dissolved in a CHCl$_3$/MeOH mixture, the solution was evaporated under reduced pressure and the resulting thin film was dried under high vacuum for 2 h. The lipid film was hydrated in 1.2 mL of phosphate buffer (10 mM sodium phosphate, pH=6.4, 75-100 mM M$_n$X, M=N$^+$, K$^+$, X=Cl$^-$, SO$_4^{2-}$, n=1,2) containing 10 μM HPTS (pyranine, 8-hydroxypyrene-1,3,6-trisulfonic acid trisodium salt) for 40 min. During hydration, the suspension was submitted to 5 freeze-thaw cycle (liquid nitrogen, water at rt). The large multilamellar liposome suspension (1 mL) was submitted to high-pressure extrusion at rt (21 extrusions through a 0.1 μm polycarbonate membrane afforded a suspension of LUVs with an average diameter of 100 nm). The LUV suspension was separated from extravesicular dye by size exclusion chromatography (SEC) (stationary phase: Sephadex G-10, mobile phase: phosphate buffer) and diluted with the same phosphate buffer to give a stock solution with a lipid concentration of 11 mM (assuming 100% of lipid was incorporated into liposomes).

pH-state transport assays. Typically, 100 μL of HPTS-loaded vesicles (stock solution) was suspended in 1.9 mL of the corresponding buffer and placed into a fluorimetric cell. The emission of HPTS at 510 nm was monitored with excitation wavelengths at 403 and 460 nm simultaneously. During the experiment, 20 μL of a 0-10 mM DMSO solution of the compounds of interest was added (through an injection port), followed by injection of 21 μL of 0.5 M aqueous NaOH. Addition of the NaOH resulted in a pH increase of approximately 1 pH unit in the extravesicular buffer. Maximal possible changes in dye emission were obtained at the end of each experiment by lysis of the liposomes with detergent (40 μL of 5% aqueous Triton X100). The final transport trace was obtained as a ratio of the emission intensities monitored at 460 and 403 nm and normalized to 100% of transport. Pseudo-first order rate constants were calculated from slopes of the plot of $\ln([H^+_{ins}]-[H^+_{out}])$ versus time, here $[H^+_{ins}]$ and $[H^+_{out}]$ are the intravesicular and extravesicular proton concentrations, respectively. The $[H^+_{out}]$ was assumed to remain constant over the course of the experiment, while $[H^+_{ins}]$ values were calculated for each point from the HPTS emission intensities according to the calibration equation $pH=1.1684 \cdot \log(I_o/I_I)+6.9807$, where $I_o$ is the emission intensity with excitation at 460 nm and $I_I$ is emission intensity with excitation at 403 nm. The calibration was performed by measuring the HPTS emission intensities and the pH values of a 470 pM HPTS solution in 10 mM phosphate buffer containing 100 mM NaCl (see FIG. s3). The absolute values for rate constants varied depending on the age of the vesicular solution and the actual stock solution of liposomes used. The ratios between absolute values of rate constants obtained from experiments on the same batch of liposomes, however, did not vary significantly.

Analysis of pH changes in the liposomes experiencing a Cl⁻ gradient. a) Outwardly directed gradient of Cl:HPTS-loaded vesicles (100 μL of the stock solution), filled with a saline phosphate buffer (10 mM sodium phosphate, pH 6.4, 100 mM NaCl) were suspended in 1.9 mL of an isosmotic phosphate sulfate buffer (10 mM sodium phosphate, pH 6.0, 75 mM $Na_2SO_4$) and placed into a fluorimetric cell. The emission of HPTS at 510 nm was monitored with excitation wavelengths at 403 and 460 nm simultaneously. During the experiment, 20 μL of a 0-2 mM DMSO solution of the compound of interest was added through an injection port. Intravesicular pH values were obtained as described for pH-stat transport assays. At the end of experiment, the aqueous compartment of liposomes was equilibrated with extravesicular solution by lysis of liposomes with detergent (40 μL of 5% aqueous Triton X100). b) Inwardly directed gradient of Cl:HPTS-loaded vesicles (100 μL of the stock solution), filled with a isoosimomolar sulfate phosphate buffer (10 mM sodium phosphate, pH 6.0, 75 mM $Na_2SO_4$) were suspended in 1.9 mL of an isosmotic phosphate saline buffer (10 mM sodium phosphate, pH 6.4, 100 mM NaCl) and placed into a fluorimetric cell. Further analysis was conducted as described for the case of an outwardly directed gradient of Cl⁺. Analysis of the electrostatic potential on the surface of liposomes. LUVs (100 μL of stock solution, 100 mM KCl inside and outside or 75 mM $Na_2SO_4$ inside and outside) were suspended in 1.9 mL of 100 mM NaCl buffer containing 60 nM safranin O (a potential-sensitive dye). Safranin O emission was monitored at 580 nm with excitation at 520 nm. During the course of the experiment, 20 μL of a 0-0.12 mM DMSO solution of valinomycin or 0-2 mM of 3-8 DMSO solution was added. Experiments were completed by injection of 20 μL of 1 mM aqueous solution of the defect-inductive peptide melittin.

Cl NMR Transport Assays

Liposome Preparation for $^{35}Cl$ NMR Assays. Egg yolk L-α-phosphatidylcholine (1.0 mg/mL EYPC ethanol solution, 250 μL, 329 μmol) was dissolved in a $CHCl_3$/MeOH mixture, the solution was evaporated under reduced pressure and the resulting thin film was dried under high vacuum for 2.5 h. The lipid film was hydrated in 1.0 mL of phosphate buffer (9:1 $H_2O:D_2O$, 10 mM sodium phosphate, pH=5.4, 100 mM NaCl) containing 10 mM $CoCl_2$ ($^{35}Cl$ shift reagent) for 40 min. During hydration, the suspension was submitted to 5 freeze-thaw cycles (liquid nitrogen, water at rt). The giant liposome suspension (1 mL) was submitted to high-pressure extrusion at rt (41 passes through a 5.0 μm polycarbonate membrane). The giant vesicle suspension was partially separated from extravesicular $CoCl_2$ by size exclusion chromatography (SEC) (stationary phase: Sephadex G-25, mobile phase: 9:1 $H_2O:D_2O$, 10 mM sodium phosphate, pH=6.4, 75 mM $Na_2SO_4$) to give 12 mL of the giant vehicle suspension (NaCl/$CoCl_2$ inside, $Na_2So_4$ outside). The suspension was concentrated to approximately 1.5 mL by centrifugation at 14,000 rpm for 30 sec followed by removal of the non-vesicle containing buffer (note, this step further decreased the $CoCl_2$ extravesicular concentration). The 1.5 mL suspension was diluted to 3 mL with the $Na_2SO_4$ buffer (9:1 $H_2O:D_2O$, 10 mM sodium phosphate, pH=6.4, 75 mM $Na_2SO_4$) to give a suspension that was 88 mM in EYPC (assuming 100% of lipid was incorporated into liposomes and estimating 20% was lost in purification/concentration). This suspension was used directly in $^{35}Cl$ NMR transport assays.

$^{35}Cl$ NMR Measurements. All $^{35}Cl$ NMR spectra were recorded on a Bruker DRX500 instrument operating at 49.0023 MHz for the $^{35}Cl$ resonance and chemical shift values are reported in ppm relative to 25 mM NaCl in $D_2O$ at 0 ppm (external standard). A 5 mm broad band probe was used. A 90° pulse width (22 μs), acquisition time of 200 ms with no delay between pulses, and a sweep width of 8.2 kHz was used in all experiments. The number of transients ranged from 3,000 to 20,000. For each run, 400 μL of the giant vesicle suspension was placed in a 5 mm NMR tube and the instrument was locked on $D_2O$. Details of each spectrum are given in the Figure legends.

Figure 1A:
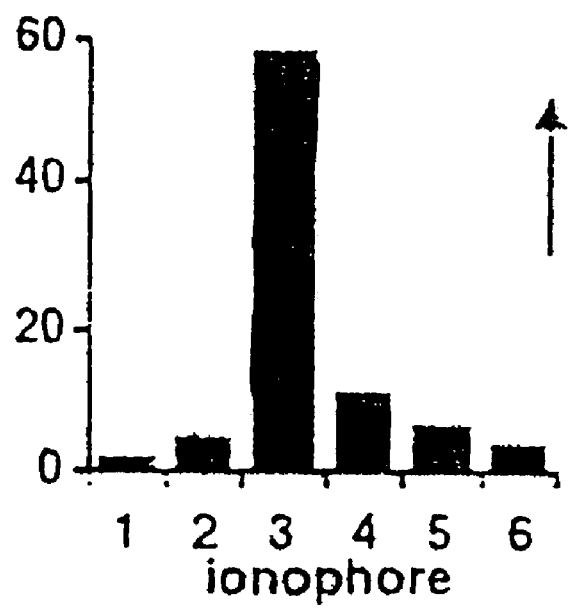

The transport activity of compounds 1-6 was evaluated by pH-star fluorescent assay. A substantial increase in transport rates with increasing chain length was observed for compounds 1-3. Monomer 1 exhibited some activity at 50 μm (10 mol % ligand to lipid ratio). Dimer 2 had moderate transport activity below 4 mol %. (20 μm). However, use of trimer 3 at concentrations as low as 0.5 mol % (5 μm) resulted in rapid exchange between extra- and intravesicular electrolytes. See FIGS. 1A and 1B.

Further elongation of the oligomer backbone resulted in some decrease of activity. Thus, tetramer 4 was generally more effective than pentamer 5 and hexamer 6.

Surprisingly, the activity trend displayed by butylamides 1-6 was found to be quite different from that reported for other ion transporters where the length of the most active compounds approached the thickness of the membrane's hydrophobic interior. While the trimer 3 was found to be generally the most active than oligomer at all concentrations, the relative transport abilities of the butylamide oligomers was found to vary with concentration. See FIG. 1B.

Importantly, compounds 2-6 were found to mediate electrolyte exchange in the presence of chloride anion. For example, in contrast to the results shown in FIGS. 1A and 1B, where NaCl extra- and intravesicular buffers were used, no transport activity was detected in liposomes symmetrically loaded with sodium sulfate even with 10 mol % of trimer 3 (50 μm). This anion dependent activity is a strong indication that amides 2-6 mediate $Cl^-$ transport across the bilayer.

EXAMPLE 1

Direct evidence for $Cl^-$ transport by trimer 3 was obtained from $^{35}Cl$ NMR.

Figure 2A:
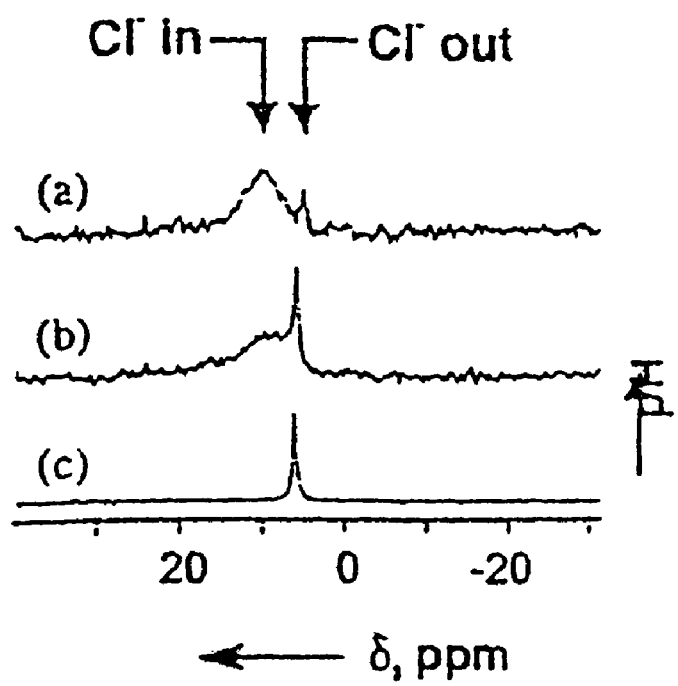
FIG. 2A illustrates $^{35}Cl$ NMR spectra of a suspension of giant vesicles (29 mM EYPC, 100 mM NaCl, 10 mM $CoCl_2$, 10 mM $Na_nH_{3-n}PO_4$, n=1, 2 pH 5.3) suspended in 75 mM $Na_2SO_4CO^{3+}$-free buffer ($Na_nH_{3-n}PO_4$, n=1, 2, pH spectra correspond to a) giant vesicles in the absence of 3, b) giant vesicles after application of 2 mol % 3 in DMSO, c) vesicles after lysis with Triton X-100.

Vesicles containing NaCl and $Co^{2+}$ were suspended in a $Co^{2+}$-free $Na_2SO_4$ buffer. The paramagnetic $Co^{2+}$ caused a downfield shift and broadening of the $^{35}C$ NMR signal. A separate broad signal for $Cl^-$ inside the liposomes was observed along with a smaller and sharper peak for residual extravesicular $Cl^-$ (FIG. 2A, top). The enhancement of the extravesicular $Cl^-$ peak upon addition of trimer 3 was attributed to outward $Cl^-$ transport by 3 (FIG. 2A, middle).

EXAMPLE 2

The ability of compounds 1-6 to alter the pH in liposomes under a $Cl^-$ gradient was tested. Trimer 3 was found to be the most active compound in the series tested.

Application of 4 mol % of trimer 3 to a suspension of NaCl-loaded liposomes in a $Na_2SO_4$ buffer generated a pH gradient of approximately are pH unit within 1.5 minutes. This pH gradient remained stable for 5 minutes until the liposomes were lyzed. Tetramer 4 was less active than trimer 3. Application of an equal amount to the tetramer 4 gave rise to the same pH gradient, but only after 4.5 minutes. Alkanization of the vesicular compartment was observed or dimer 2, pentamer 5 and hexamer 6. The resulting pH gradients, however, did not reach the maximum even 7 minutes after addition of the compounds.

However, as noted above, the compounds of the present invention may have a calixarene structure.

The synthesis of calix[4]arene amides is known and described in the literature as noted in footnote 1.

EXAMPLE 3

In this example, calix[4]arene tetrabutylamide was evaluated as described below. It was observed calix[4]arene tetrabutylamide 2 binds HCl in solution, forms ion channels in a lipid bilayer, and effectively transports HCl across liposomal and cell membranes. Also, the analogous calix[4]arene tetramethylamide I self-assemblies in the presence of HCl to form ordered arrays containing chloride-filled and water-filled channels. By comparing ion binding and transport properties of calix[4]arene tetrabutylamide 2 with those of its analogues 1, 3 and 4, it was determined that the compound's hydrophobicity, the amide's substitution pattern and the calixarene macrocyclic framework facilitate ion transport. The evidence points toward a self-assembled channel being formed by calyx[4]arene tetrabutylamide 2 in an anion-dependent process.

Calix[4]arene tetramethylamide 1, tetrabutylamide 2, and octabutylamide 3 were prepared by coupling the appropriate amine with calyx[4]arene-1, 3-alt tetracid chloride. Synthesis and characterization of 1-3 are detailed below.

Calix[4]arene tetrabutylamide 2 transports ions across the bilayer without cation selectivity, whereas calix[4]arene tetramethylamide 1 does not effectively mediate ion transport. The ability of 1 and 2 to mediate ion flux across a lipid bilayer was studied fluorimetrically. A solution of 1 or 2 was added to a suspension of EYPC large unilamellar vesicles (LUVs) containing the pH-sensitive dye pyranine. An NaOH solution was added to the extravesicular buffer to create a gradient of approximately one pH unit. The resulting electrostatic potential, caused by proton efflux from the liposomes, can be compensated by cation influx or anion efflux, as mediated by the exogenous ligand. Ion transport across the membrane was signaled by the increase in relative fluorescence that accompanied the rise in intravesicular pH.

The polyanionic pyranine is known to adsorb strongly to positively charged vesicles. Pyranine also adsorbs to some extent to neutral liposomes such as EYPC. The fluorescence traces, which measure the ratio of deprotonated to protonated forms of the dye (see Experimental Section), register a response that is directly proportional to pH. In this way, dye absorption to the internal surface of the vesicles does not interfere with the pH measurements. The amount of dye adsorbed to the outer surface of EYPC LUVs is estimated by analyzing the burst response upon base addition. This response generally never exceeded 15% of the total fluorescence change observed.

TABLE 1

Initial Pseudo-first Order Transport Rate Constants ($\times 10^{-3}$ $s^{-1}$) for Intravesicular and Extravesicular Electrolyte Exchange in the Presence of 5 μM of 2 or 3 and Different Salts.

| Salt transporter | NaCl | KCl | CsCl | $Na_2SO_4$ |
| --- | --- | --- | --- | --- |
| $2^a$ | $6.8^{b,c}$ | $6.4^{b,c}$ | $7.7^{b,c}$ | $1.1^{b,d}$ |
| $3^a$ | $19^{b,c}$ | $12^{b,c}$ | $5.4^{b,c}$ | $9.1^{b,d}$ |

Figure 2B:
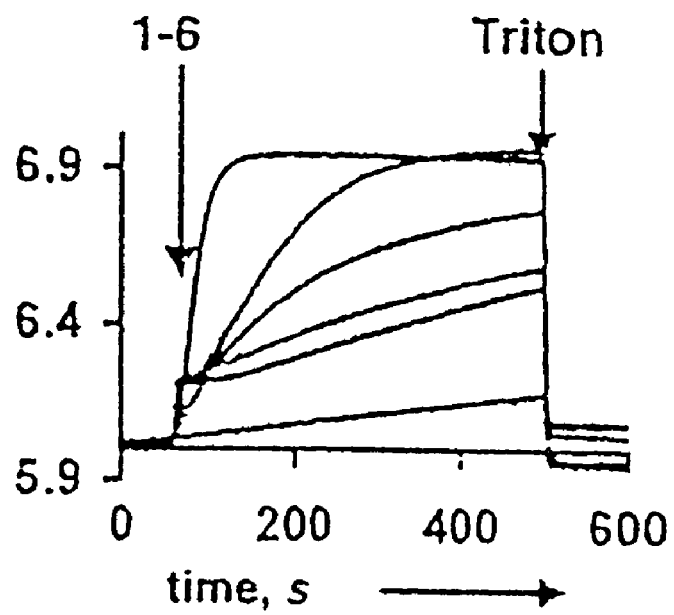
FIG. 2B illustrates alkanization of the vesicular aqueous compartment upon application of compounds 1-6 to a suspension of NaCl-containing vesicles in isosmomolar $Na_2SO_4$ buffer. Concentration of compounds 1-6 in the vesicular suspension was 20 μm (4 mol %). Legend for traces denotes use of oligocompounds 1, 2, 3, 4, 5, 6.
Figure 3:
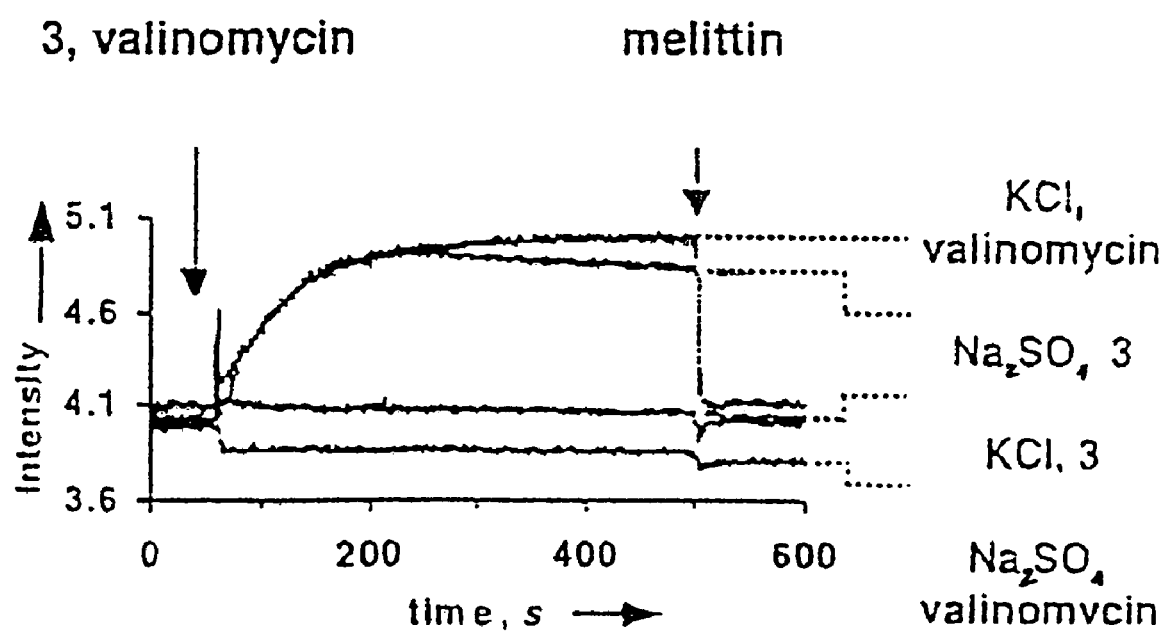
FIG. 3 illustrates liposome potential assays. Suspension of EYPC LUVs in phosphate buffer was used (10 m M $Na_n$ $H_{3-n}$ $PO_4$, n=1, 2, pH 6.4, 100 m M KCl or 75 m M $Na_2$ $H_{3-n}$ $PO_4$, n=1, 2, pH 6.4, 100 m M KCl or 75 m M $NA_2$ $SO_4$ inside and 100 m M NaCl, 60 nM safranin O, ex 480 nm, em 520 nm, outside). Legend for trace denotes the formation of potential in: —KCl vesicles upon application of valinmycin·$Na_2SO_4$ vesicles upon application of 3, —KCl vesicles upon application of 3, —$Na_2SO_4$ vesicles upon application of valinomycin. The potentials were reached at the end of each experiment by injection of 20 μl of 1 m M aqueous solution of the defect-including peptide melittin.

[a]20 μL of 0.5 mM THF solution of the compound was added to 2 mL of a 0.5 mM LUV suspension.
[b]Rate constants were determined as described in the Experimental Section. Values are not corrected for unmediated electrolyte exchange. The accuracy of measurements was ±15% for experiments using the same set of liposomes.
[c]100 mM NaCl, 10 mM phosphate buffer, pH 6.4 inside; 100 mM MCl, M = Na, K, or Cs, 10 mM phosphate buffer, pH 7.4 outside, after pH pulse. Note that values are not directly comparable because of different ion gradients.
[e]100 mM $Na_2SO_4$. 10 mM phosphate buffer, pH 6.4 inside; 100 mM $Na_2SO_4$. 10 mM phosphate buffer, pH 7.4 outside, after pH pulse.

in the course of the experiments. The slower phase of fluorescence increase is due to the rise in intravesicular pH as calixarene 2 transports ions across the EYPC membrane. It is the rate constant for this second phase that we report in Table 1. Furthermore, negative controls shown in FIG. 2 clearly indicate that there is little fluorescence increase in the absence of calixarene 2.

Calix[4]arene tetramethylamide 1 showed little transport activity in the presence of extravesicular $Na^-$, $K^-$, or $Cs^-$ chloride at ligand lipid ratios of up to 1:20, whereas rapid exchange of intra-and extravesicular electrolytes was observed in the presence of calix[4]arene tetrabutylamide 2 at a ligand:lipid ratio of 1:100. These fluorescence assays in buffers containing $Na^-$, $K^-$, or $Cs^-$ indicated that ion transport mediated by 2 was nonselective toward the cation. The reduced activity for tetramethylamide 1 can be attributed to its lower hydrophobicity with respect to tetrabutylamide 2.

Calix[4]arene tetrabutylamide 2 does not induce defects into the bilayer membrane but provides selective transport of $Cl^-$ over $HSO_4$. Calix[4]arene tetrabutylamide 2 may transport ions across LUVs by inducing membrane defects, by uniport of ions, or via cotransport of ion pairs ($H^{31}$, $M^-$ or $OH^-/A^-$ antiport and $H^+/A^-$ or $M^+/OH^-$ symport mechanisms are possible). The lytic potential of 2 was evaluated using a dye release assay. The self-quenching dye calcein loses 95% of its fluorescence emission at concentrations above 100 mM. 2. A suspension of LUVs containing 120 mM calcein showed no fluorescence enhancement upon dilution with an isoosmotic buffer containing 2 (5-100 µM, 1-20 mol % ligand, relative to total lipid concentration, data not shown). This calcein experiment indicates that 2 does not induce membrane defects.

Secondary amides can interact with anions and cations, plausibly explaining why calix[4]arene tetrabutylamide 2 could transport either ion type. Since the transport activity of calix[4]arene 2 was cation-independent, we tested whether ion transport mediated by 2 might be anion dependent. Standard fluorescence assays were conducted with sodium sulfate-filled LUVs suspended in an isotonic solution. Unlike for chloride-containing solutions, experiments in sulfate buffers revealed that the pH-induced ion flux across the membrane was not mediated by 5-50 µM concentrations of 2. This pronounced $Cl^-$ over $HSO_4^-$ transport selectivity (Table 1) indicates that 2 preferably functions as a $Cl^-$ transporter.

Figure 4:
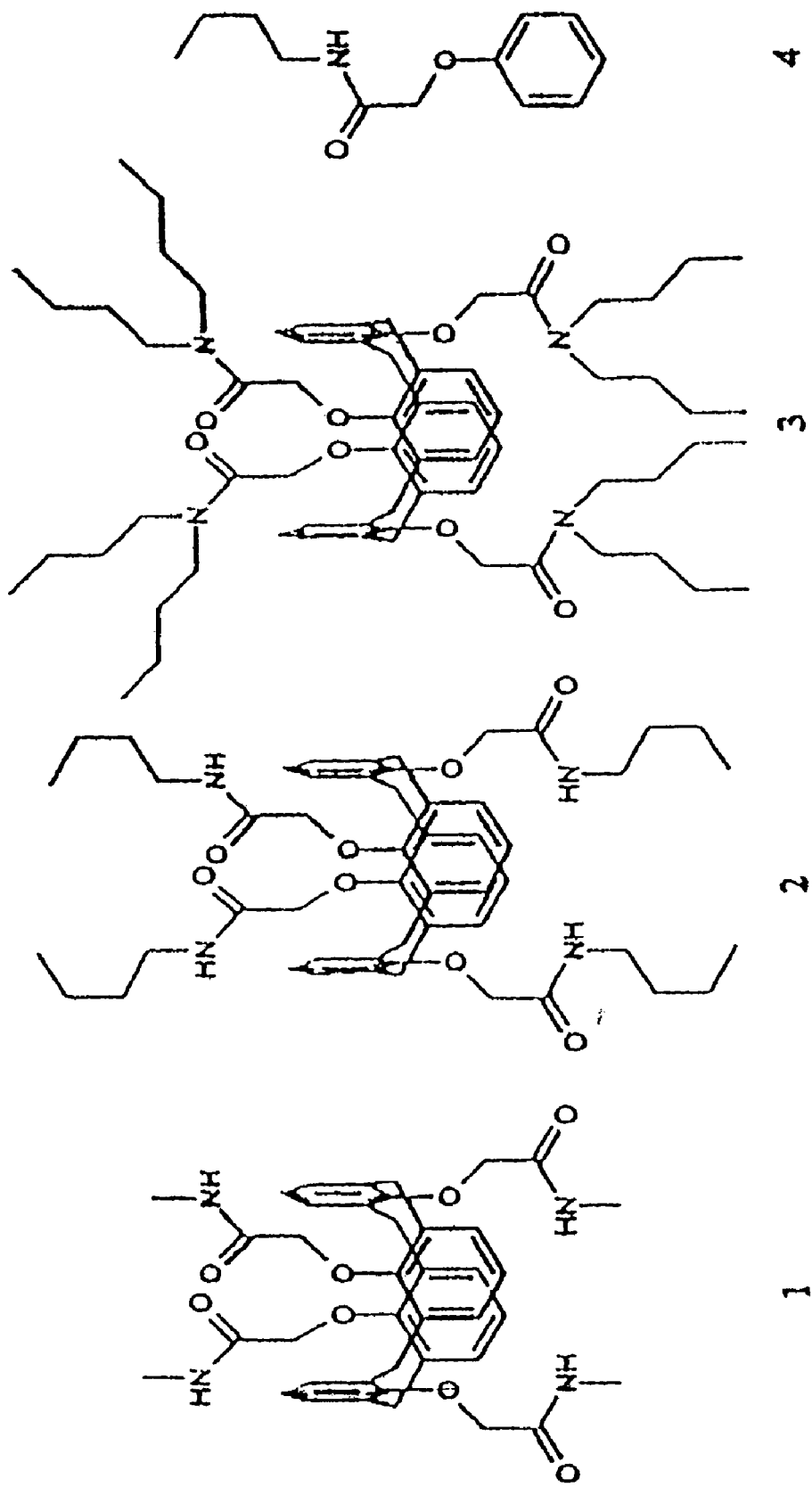
FIG. 4 illustrates the structures of calixarene compounds 1-4.
Figure 5A:
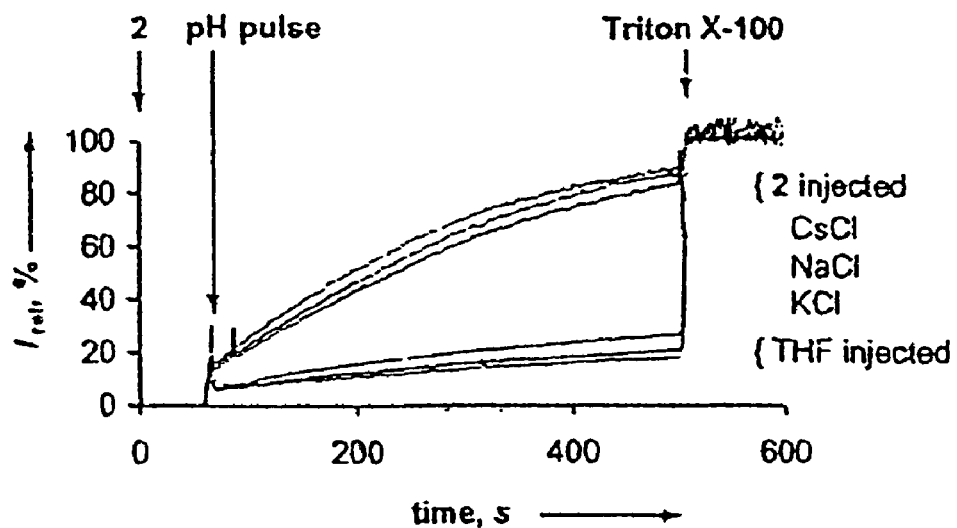
FIG. 5(A) illustrates liposome transport assay results with 2, calix[4]arene tetrabutylamide, in the presence of NaCl, KCl and CsCl. Suspensions of EYPC LUVs containing the pH-sensitive dye pyranine in a phosphate buffer were used. The intravesicular solution contained 10 mM sodium phosphate, pH 6.4, 100 mM NaCl and the extravesicular solution contained 10 mM sodium phosphate, pH 6.4, 100 mM MCl (M=NA, K, Cs). At t=0s, 20 μL of a 0.5 mM solution of calix[4]arene tetrabutylamide in the THF was added (top three curves) to give 1:100 2:lipid molar ration or 20 μL. THF was added (bottom three curves). At t=60 s, 21 μL of a 0.5 M NaOH solution was added. At t=500 s, 40 μL of 5% Triton X-100 was added. Counting from top to bottom, traces 1 and 4 correspond to the solutions containing 100 mM CsCl, traces 2 and 6 correspond to the solutions containing 100 mM NaCl, and traces 3 and 5 correspond to solutions containing 100 mM KCl buffer.
Figure 6:
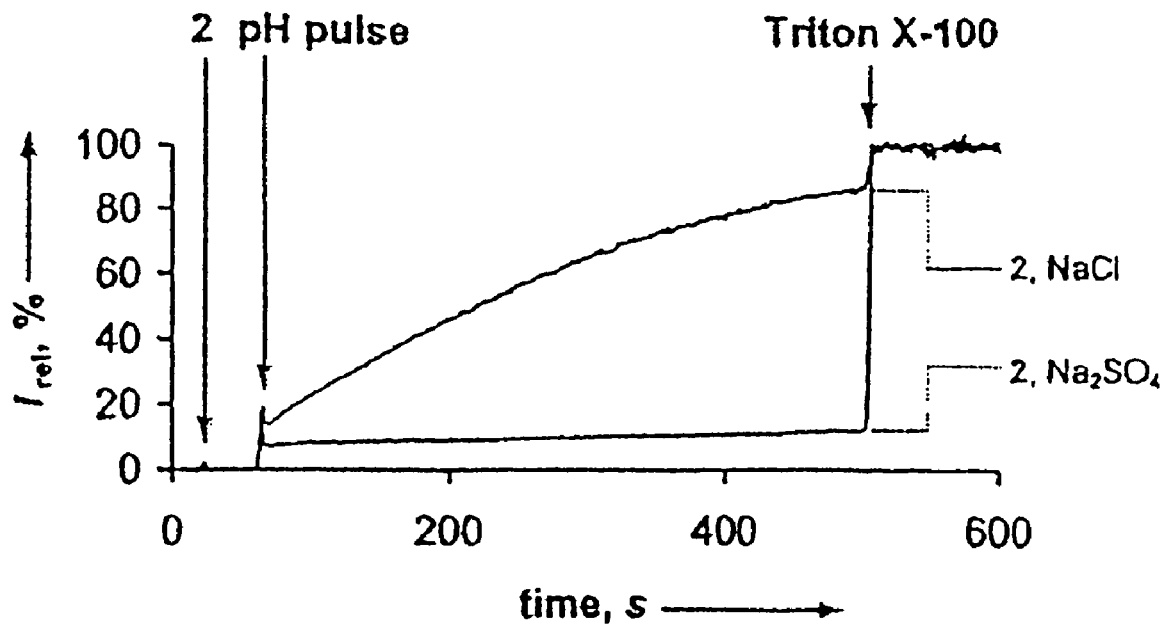
FIG. 6 illustrates the results of transport assays with calix[4]arene tetrabutylamide in the presence of extravesicular buffers containing NaCl (top trace) and $Na_2SO_4$ (lower trace). Suspensions of EYPC LUVs containing the pH-sensitive dye pyranine in a phosphate buffer were used. At t=20 s, 20 μL of a 500 μm of calix[4]arene tetrabutylamide in THF was added to 1.95 mL of LUV suspension to give 1:100 calix[4]arene amide: lipid molar ratio. At t=60 s, 21 μL of 0.5 μ NaOH was added to change the extravesicular pH from 6.4 to 7.4. At t=500 s, 40 μL of 5% Triton X-100 was added. No significant transport in the $Na_2SO_4$ buffer was observed even in the presence of up to 50 $Na_2SO_4$ μm of calix[4]arene tetrabutylamide.
Figure 5B:
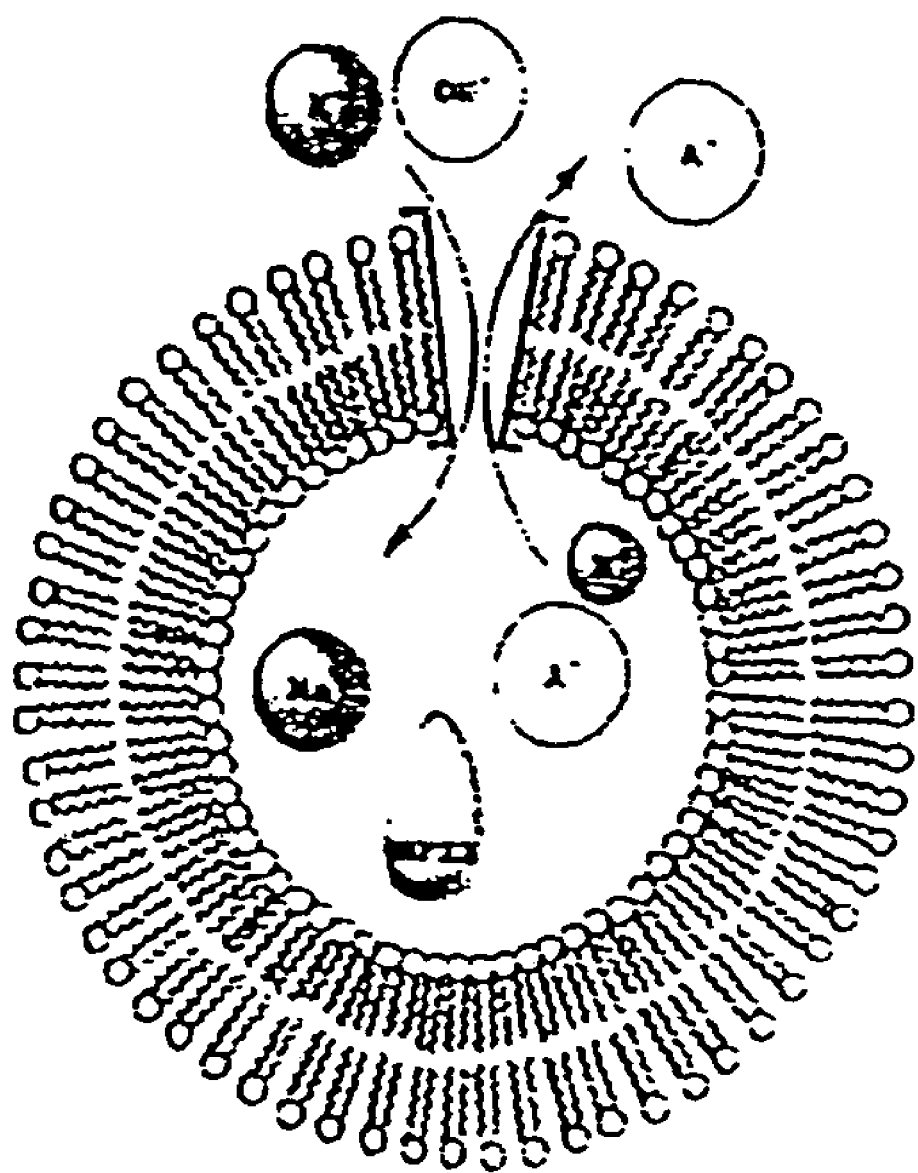
FIG. 5(B) illustrates a schematic representation of transport experiments. A pH gradient results from addition of extravesicular NaOH solution. The charge caused by $H^+$-efflux or $OH^-$ influx is compensated by cation influx or anion efflux, as mediated by the exogenous ligand, calix[4]arene tetrabutylamide. The increase in intravesicular pH, monitored by the entrapped pH-sensitive dye, HTPS reflects the electrolyte exchange rate.
Figure 7:
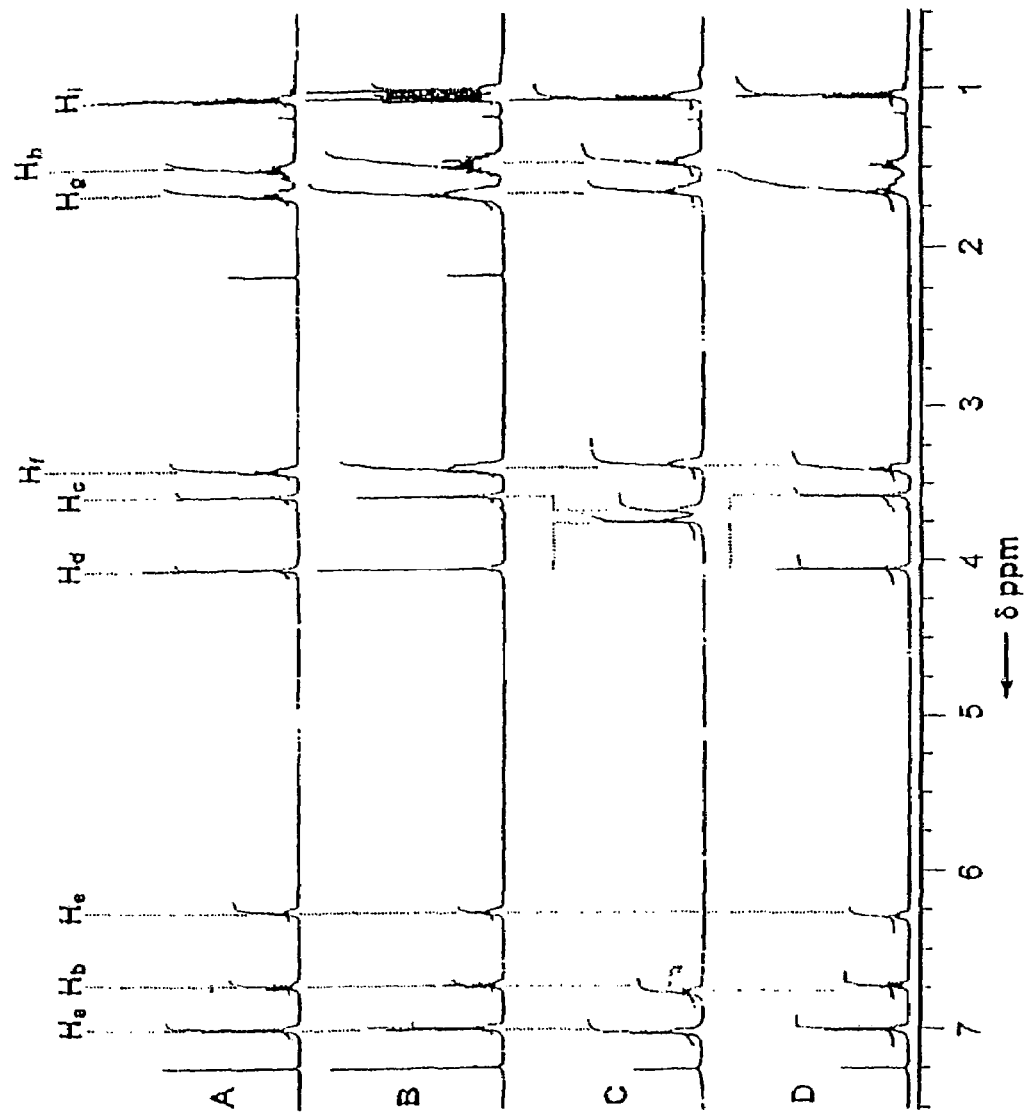
FIG. 7 illustrates a series of $^1N$ NMR spectra (400 mHz, $CDCl_3$, 22° C.) of calixarene tetrabutylamide in the presence of different species: (A) the compound alone (5 mm); (B) the compound with 1 equiv. of $Bu_4NCl$; (C) the compound after washing $CDCl_3$ solution of the compound with an aqueous solution of 0.5 m HCl; (D) after washing $CDCl_3$ solution of the compound with an aqueous solution of 0.5 M $H_2SO_4$.
Figure 8:
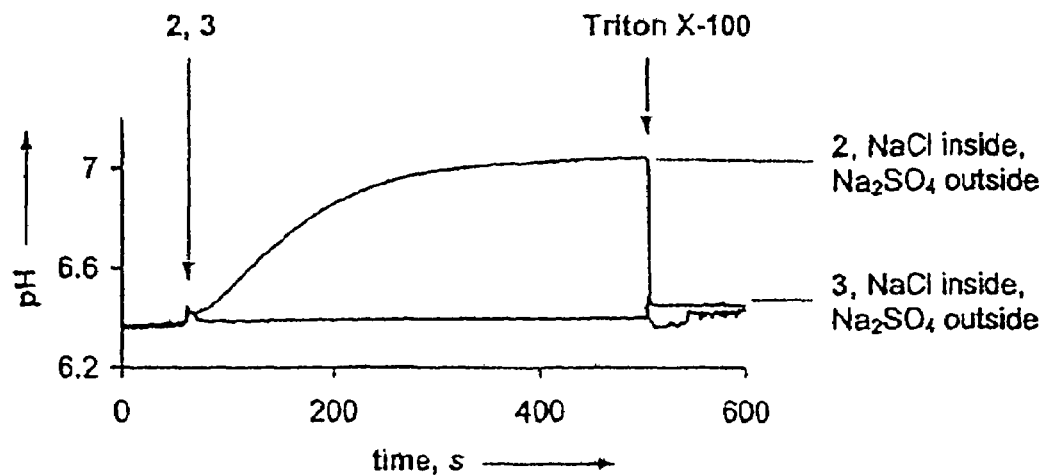
FIG. 8 illustrates changes in intravesicular pH upon addition of calixarene tetrabutylamide and calixarene octabutylamide to $NaCl^+$ loaded vesicles suspended in a sulfate phosphate buffer (emission of HPTS is used to monitor the pH changes in LUVs). At t=60 s, 20 μL of 500 μM of calixarene tetrabutylamide 2 (top trace) or the octabutylamide 3 (bottom trace) was added to 1.95 mL of a LUV suspension to give 1:100 ligand:lipid molar ratio. At t=500 s, 40 μL of 5% Triton X-100 was added. Intravesicular pH values were obtained as a function of the ratio of HPTS emission intensities at 510 nm, when excited at 403 and 460 μm. The calibration was performed by measuring the HPTS emission intensities and the pH values of a 4.70 nm HPTS solution in 10 mM phosphate buffer containing 100 mM NaCl. The calibration equation obtained (pH=1.1684×log $(I_0I_1)$+6.9807, r=0.998, where $I_0$ is the emission intensity with excitation at 403 nm) was used to convert the emission intensities into actual pH values.

$^1$H NMR experiments show that calix[4]arene tetrabutylamide 2 binds HCl. To obtain evidence for $Cl^-$ binding by 2, $^1$H NMR experiments were run in $CDCl_3$ using n-$Bu_4$-NCl and HCl as $Cl^-$ sources. Anion receptors usually show chemical shift perturbation upon anion complexation, particularly for amide NH protons that hydrogen bond to the anion. Surprisingly, no changes in the $^1$H NMR spectrum of the secondary amide 2 in $CDCl_3$ were observed upon addition of n-$Bu_4$-NCl. This lack of spectral changes indicates that 2 does not bind strongly to the "naked" $Cl^-$ anion, even in this nonpolar solvent. Calix[4]arene tetrabutylamide 2 does, however, bind HCl. Thus, shaking a $CDCl_3$ solution of 2 with aqueous HCl led to disappearance of the amide NH proton and a significant upfield shift of the $OCH_4$-C(O) protons (FIG. 4c). The NMR spectral changes of 2 induced by HCl extraction were not simply due to acid treatment, since washing a $CDCl_3$ solution of 2 with a $H_2SO_4$ solution did not cause any changes.

These $^1$H NMR experiments indicate that calix[4]arene tetrabutylamide 2 is a ditopic HCl receptor, since both $H^+$ and $Cl^-$ are needed to induce spectral changes. These NMR data for 2 are consistent with the LUV transport results, where efficient ion transport across the membrane was observed in the presence of $Cl^-$ but not $H_2SO_4$. The combined fluorescence and NMR results lead us to conclude that calyx[4]arene tetrabutylamide 2 supports ion transport across LUVs in an anion-dependent fashion by either an $H^+/Cl^-$ symport or a $Cl^-/OH^-$ antiport mechanism.

Calix[4]arene tetrabutylamide 2 mediates effective $H^+/Cl^-$ transport across bilayer membranes. With NMR evidence that calix[4]arene tetrabutylamide 2 binds HCl in a hydrophobic environment it was determined that 2 might transport HCl across LUVs. Previously, we showed that a pH gradient across $Cl^-$ filled vesicles was collapsed by addition of 2 (FIG. 2a). We evaluated the reverse situation by monitoring the intravesicular pH of LUVs experiencing a $Cl^-$ gradient.

When a suspension of LUVs filled with saline phosphate buffer (100 mM NaCl, 10 mM sodium phosphate, pH 6.4) and suspended in isosmotic $Na_2SO_4$ buffer (75 mM $Na_2SO_4$. 10 mM sodium phosphate, pH 6.4) was treated with 2, we observed a rapid increase in intravesicular pH. The pH reached its maximum 250 s after addition of 2 and held constant until the liposomes were lysed with detergent.

These results are consistent with an $H^+/Cl^-$ symport or $Cl^-/OH^-$ antiport process. In effect, compound 2 moves $H^-$ along with $Cl^-$ down the chloride gradient, consequently building a pH gradient across the membrane. Therefore, NaCl filled vesicles lose $Cl^-$ and $H^+$ upon addition of 2 and become more alkaline.

The secondary amide NH and the core aromatic ring framework, in this case the calix[4]arene framework, are essential for the HCl transport activity of 2. Calix[4]arene octabutylamide 3 was used as a negative control for tetrabutylamide 2, as the lack of amide NH protons in 3 would preclude $Cl^-$ binding. Instead, 3 should be a cation ionophore, much like tetrakis(diethylcarbamoylmethoxy)-p-tert-butylcalix[4]arene-1,3-alt that coordinates cations in the solid-state and solution. To confirm that 3 binds $Na^+$, sodium picrate extraction in $CDCl_3$ was monitored by $^1$H NMR spectroscopy. Complexation of the salt by 3 was evident. Two distinct complexes were formed, corresponding to a 1:1 and a 2:1 $Na^+$:3 stoichiometry. The 1:1 complex was generated by adding 1 equiv of solid sodium picrate to a solution of 3. Binding this $Na^+$ led to a symmetry loss for 3, indicated by doubling of the $^1$H NMR peaks. Addition of further sodium picrate (up to 10 equiv) resulted in a new 2:1 complex. Binding of the second $Na^+$ cation restored the ligand's initial $D_{2d}$ symmetry, as seen by the new set of single NMR signals for this 2:1 complex. In contrast, sodium picrate extraction by calix[4]arene tetrabutylamide 2 was not detected by $^1$H NMR spectroscopy.

Ion transport assays revealed a high activity for octabutylamide 3 in NaCl buffer (k=1.9×10$^{-2}$s$^{-1}$, Table 1). Unlike 2, calix[4]arene octabutylamide 3 discriminates between monovalent cations, showing a 3.5-fold drop in rate constant when changing the extravesicular electrolyte from NaCl to CsCl (Table 1). Fluorescence assays with 3 in the presence of $Na_2SO_4$ loaded vesicles suspended in isotonic buffer indicated that 3 still mediated significant ion transport, albeit with a drop in activity (k=9.1×10$^{-3}$s$^{-1}$). In marked contrast, calix[4]arene tetrabutylamide 2 had shown essentially complete loss of transport activity when the buffer was changed from one containing NaCl to one containing $Na_2SO_4$. Further evidence for different ion transport selectivity provided by calixarene octabutylamide 3 and tetrabutylamide 2 was obtained from an experiment with NaCl-loaded vesicles suspended in isoosmotic $Na_2So_4$ solution. Addition of 3 did not result in formation of a pH gradient across the membrane.

To determine whether chloride binding and transport is an intrinsic property of calixarene 2 or a general property of hydrophobic secondary amides. N-butyl-2-phenoxyacetamide 4 was tested in the LUV transport assays. Compound 4 is amonomeric analogue of calixarene 2, bearing a secondary amide that could bind $Cl^-$, but lacking the calixarene's macrocycle. The standard fluorescence assay, even in the presence of high concentrations of 4 (50 µM) showed no ion transport across the LUV membrane. In addition, $^1$H NMR spectroscopy indicated no HCl binding by 4 in $CDCl_3$. These controls with, N-butyl-2-phenoxyacetamide 4 support the hypothesis that the calixarene's core is critical for the HCl binding and ion transport properties of 2.

Calix[4]arene tetramethylamide 1 and HCl form channels in the solid state. After failing to crystallize tetrabutylamide 2, evaluated the analogous calix[4]arene tetramethylamide 1. Whereas 1 does not transport ions efficiently across the LUC membrane, presumably due to insufficient hydrophobicity, its mode of HCl binding should be similar to that for 2. Different protocols afforded two types of 1-HCl

TABLE 2

Crystal Data and Structure Refinement for 1•HCl•3($H_2O$) and 1•HCl•$H_2O$•$CH_2Cl_2$ Complexes

| | 1•HCl•3($H_2O$) | 1•HCl•$H_2O$•$CH_2Cl_2$ |
|---|---|---|
| empirical formula | $C_{40}H_{51}ClN_4O_{11}$ | $C_{41}H_{49}Cl_{13}N_4O_9$ |
| formula weight | 799.29 | 848.18 |
| temperature | 193(2) K | 193(2) K |
| crystal system | orthohombic | monoclinic |
| space group | Fddd | P2(1)/n |
| unit cell dimensions | a = 20.9026(7)Å, α = 90° | a = 10.1237(3)Å, α = 90° |
| | b = 26.5756(9)Å, β = 90° | b = 22.7400(7)Å, β = 90° |
| | c = 27.7713(10)Å, γ = 90° | c = 17.7902(6)Å, γ = 90° |
| volume | 15426.9(9) Å$^3$ | 4064.4(2) Å$^3$ |
| Z | 16 | 4 |
| density (calculated) | 1.375 mg/m$^3$ | 1.384 mg/m$^3$ |
| absorption coefficient | 0.166 mm$^{-1}$ | 0.286 mm$^{-1}$ |
| data/restraints/parameters | 3404/3/326 | 7147/0/723 |
| goodness-of-fit on $F_2$ | 1.060 | 1.092 |
| final R indices [I > 2σ(I)] | R1 = 0.0617, wR2 = 0.1785 | R1 = 0.0431, wR2 = 0.1117 |
| R indices (all data) | R1 = 0.0851, wR2 = 0.1958 | R1 = 0.0570, wR2 = 0.1196 | single crystals whose structures were solved by X-ray crystallography (see Table 2 for data). Both solid-state structures unequivocally show that Cl$^-$ anion is hydrogen bonded to the calixarene's amide NH.

Crystals of 1-HCl-3($H_2O$), obtained by evaporation of a dichloromethane/THF solution of 1 and HCl, have a structure that consists of two-dimensional planar arrays of calixarenes held together by NH—Cl$^-$—HN hydrogen bonds in the x-direction and by C=O—H—O—H—O=C hydrogen bonds in the y-direction. A side view in the y-direction reveals a chloride-filled channel, and a side view in the x-direction reveals a water-filled channel.

Analysis of a second crystal (1-HCl—$H_2O$—$CH_2$—$Cl_2$), grown by layering aqueous HCl over a dichloromethane solution of 1, revealed a structure where two molecules of calixarene 1 are linked by oppositely directed N—Cl$^{31}$—H—O(H)$^-$H—O=C bridges to give a dimmer. Each molecule of calixarene 1 in 1-HCl—$H_2O$—$CH_2Cl_2$ retains a similar geometry as observed in the structure of 1-HCl-3 ($H_2$). The main difference in the second structure is that a hydronium cation separates Cl$^-$ from the neighboring calixarene.

Although the three-dimensional network formed by the two 1-HCl complexes is different, both crystal structures indicate that calixarene 1 uses its secondary amide groups to bind HCl. These crystal structures are relevant since they indicate that calix[4]arene 1,3-alt amides can self-assemble to give extended channels held together by hydrogen bonds to bridging Cl$^-$ anions and water.

Calix[4]arene tetrabutylamide 2 forms an ion channel. Ligand-mediated ion transport across a lipid bilayer is usually attributed to three mechanisms: defect induction, a carrier process, or channel formation. Dye-release experiments showed that 2 does not induce membrane defects. Both carrier and ion channel mechanisms for H$^+$/Cl$^-$ transport are conceivable for a ligand like calix[4]arene tetrabutylamide 2. A single molecule of 2 is certainly too small to span the membrane. But the calixarene's 1,3-alt conformation makes channel-like structures possible, particularly in the presence of bridging species. Crystal structures of the 1-HCl complexes show calixarenes held together by amide-chloride-amide, amide-water-amide, and amide-chloride-water-amide hydrogen bonds. If HCl mediated self-assembly of 2 gives similar structures in lipid membranes then such aggregates could act as ion channels. Even the shortest hydrogen-bonded unit in these structures, a calixarene dimer of ~25 Å, could conceivably span a bilayer membrane.

Since ion transport supported by 2 is not electrically silent, current across the bilayer can be detected using the voltage-clamp technique, a technique that distinguishes between channel and carrier mechanisms. Evidence for ion channels formed by calix[4]arene tetrabutylamide 2 was obtained from voltage-clamp experiments on black lipid membranes (BLMs).

Figure 9:
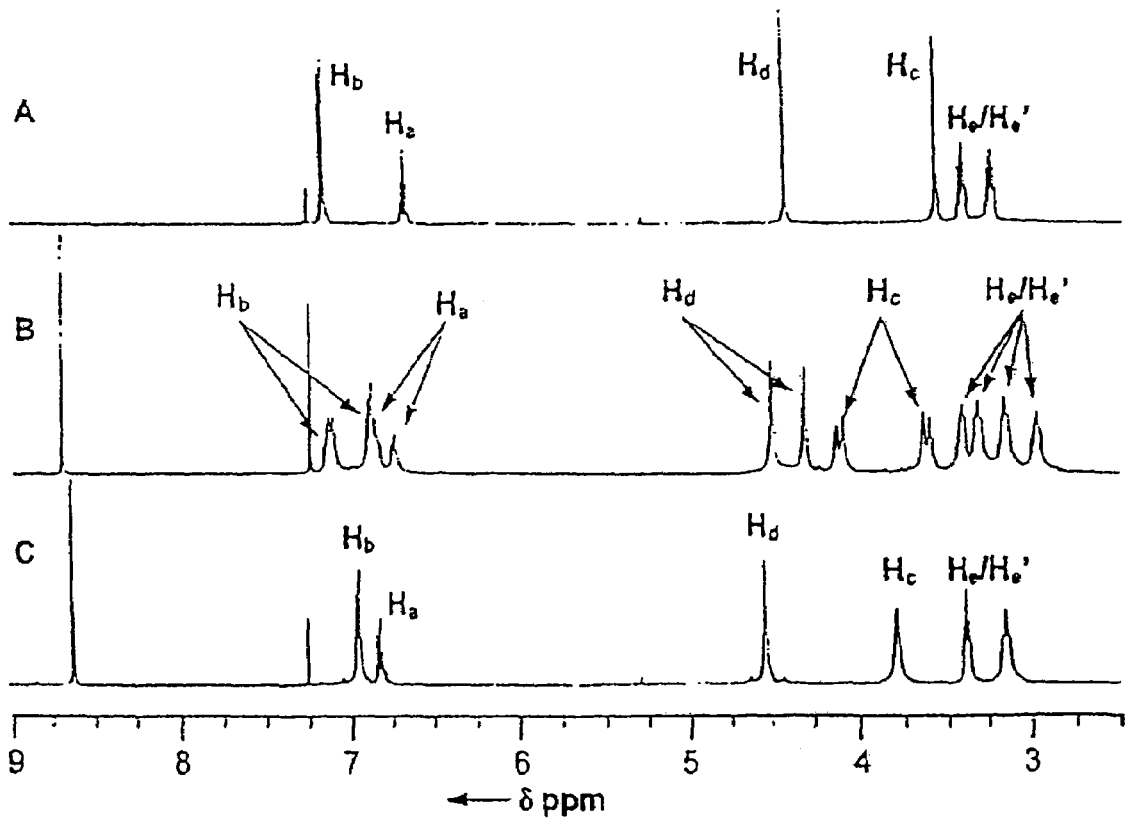
FIG. 9 $^1H$ NMR spectrum (400 MHz, $CDCl_3$, 22° C.) of (A) calixarene octabutylamide (5 mM) in $CDCl_3$, (B) the same compound after addition of 1 equiv. of NaPic. (C) the same compound after addition of 2 equiv. of NaPic. No change in this NMR spectrum was observed in the presence of up to 10 equiv. of solid NaPic.
Figure 10A:
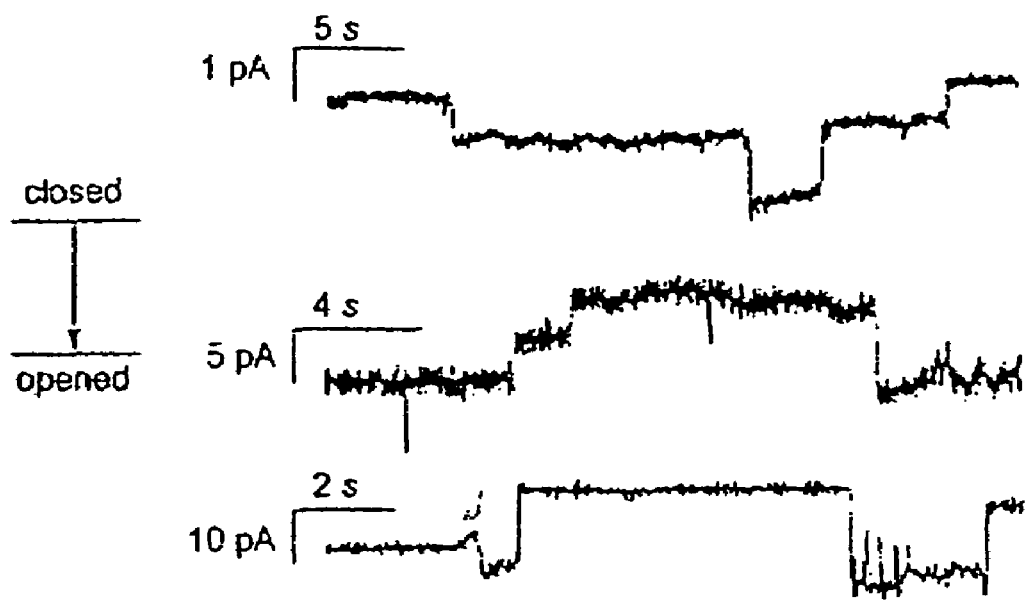
FIG. 10(A) represents current events across a BLM in voltage clamp experiments after application of calixarene tetrabutylamide 2 (2.5 μm). The voltage applied was −20 mV for all three recordings. (B) The distribution of conductance ranges observed in voltage clamp experiments with 2 acting as an ion channel.
Figure 10B:
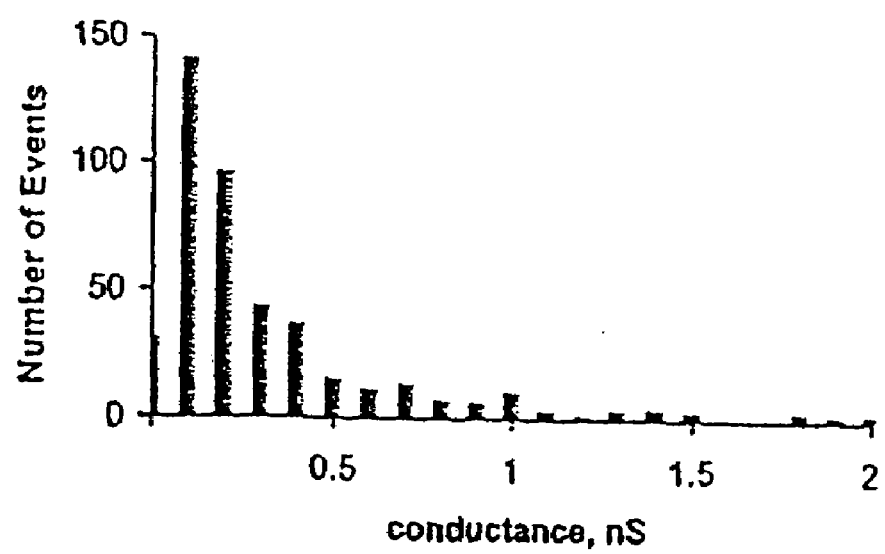
Figure 11C:
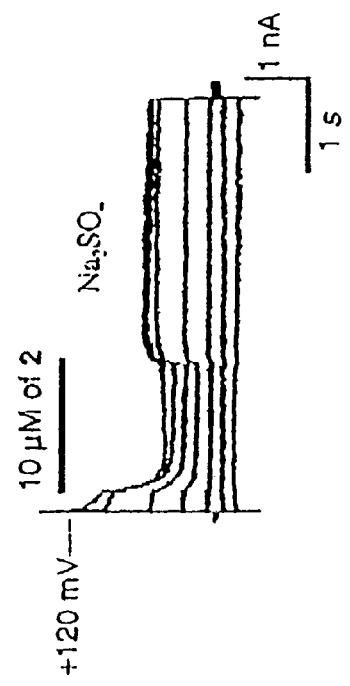
FIG. 11 illustrates voltage clamp recordings in whole cell configuration (HEK-293 cells). (A) Current across membrane after application of calixarene tetrabutylamide 2 at different voltages. From bottom to top, trace denotes currents at −120, −80, −40, 0, 40, 80 and 120 mV, respectively, with saline physiological buffer being used (B) Current across membrane in a sodium glutamate isosmotic-buffer at different voltages. The potential was varied over a range of −120 through +120 mV, with a 40 mV step. (C) Current across membrane in $Na_2SO_4$ isosmotic buffer at different voltages. The potential was varied over a range of −120 through +120 mV, with a 40 mV steps. (D) Current across the membrane at +120 mV in application/wash cycle traces from bottom to top denote current in absence of 2, current after first application of 2 (a), following by 1.5 mm lavage, second application (b), and third application (c). Trace on top denotes current after lavage without application of 2. Baselines of the first and last traces shifted for clarity, saline physiological buffer used.
Figure 11D:
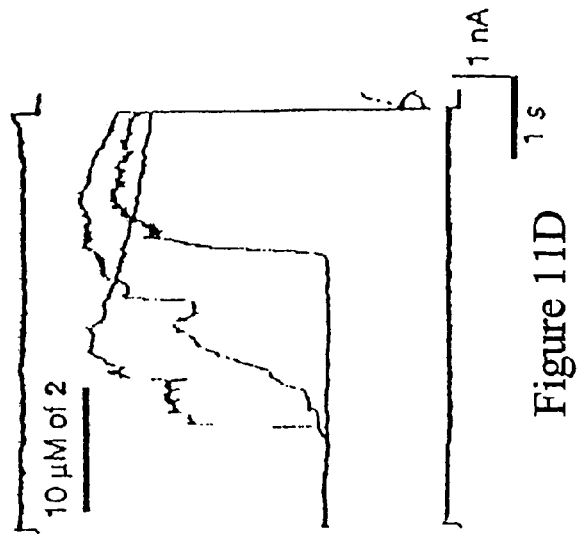
Figure 11A:
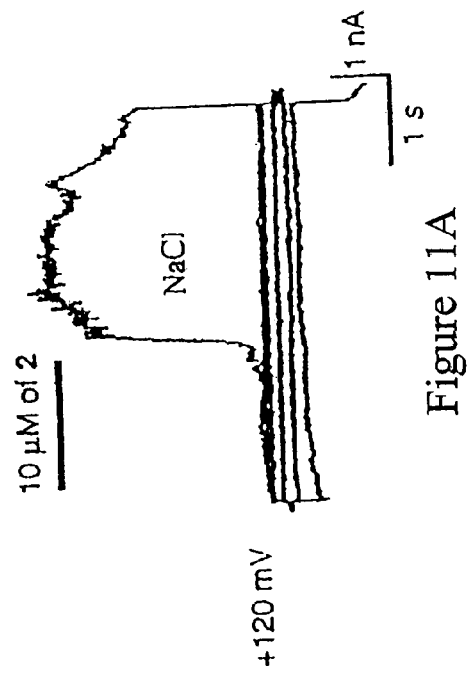
Figure 11B:
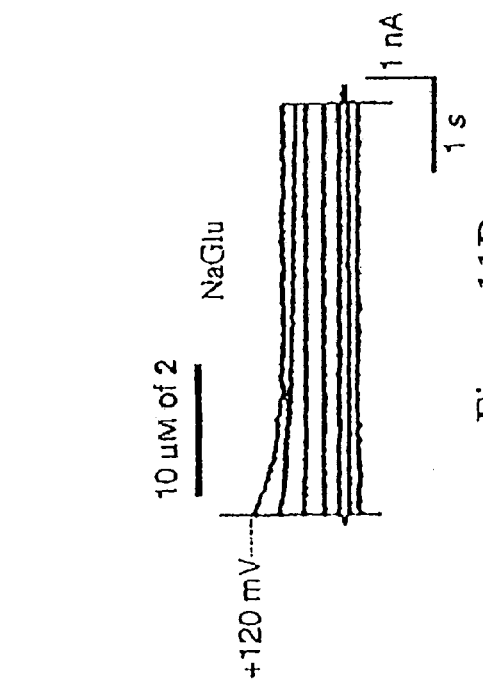
Figure 12:
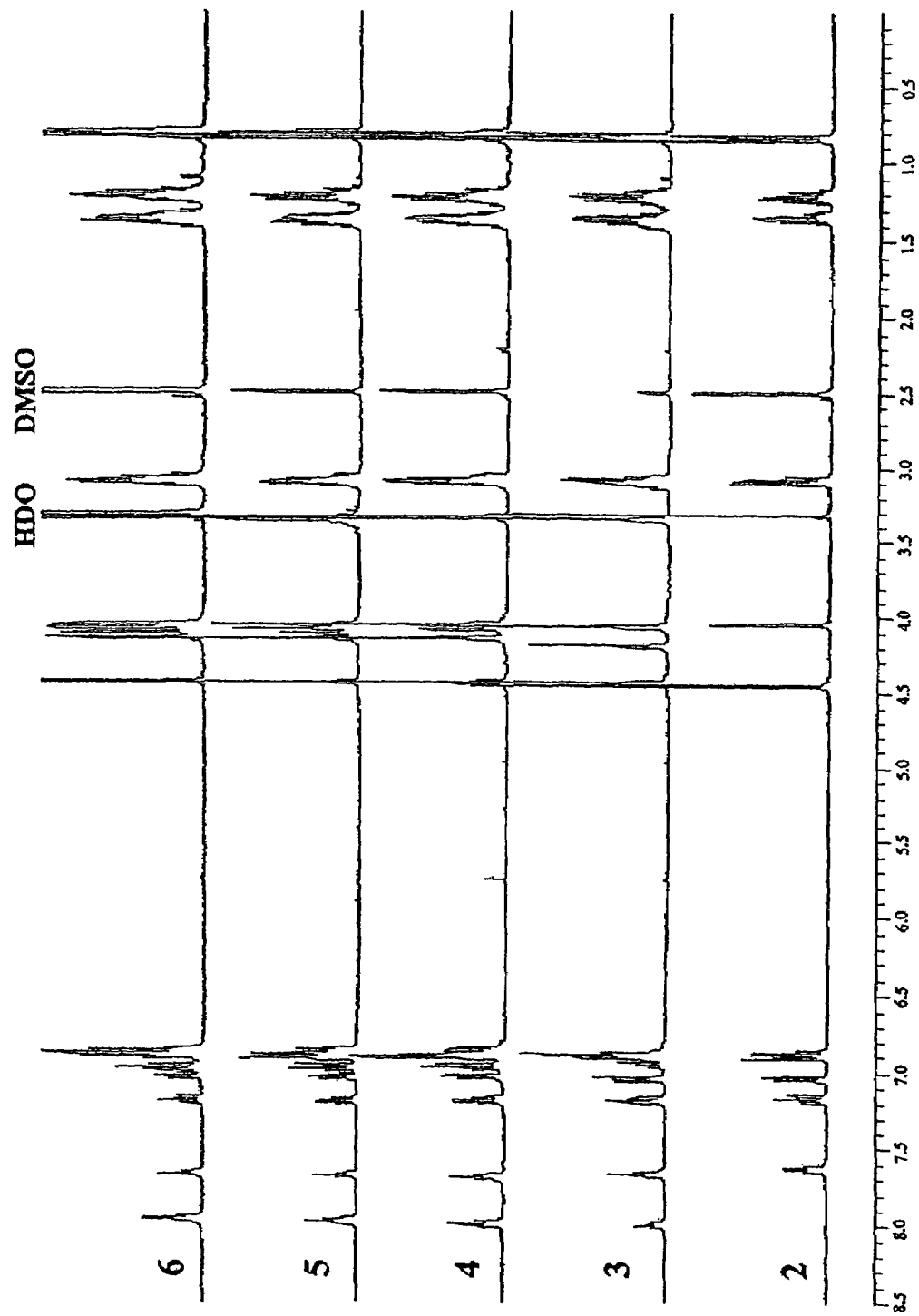
FIG. 12 illustrates a series of 400 MHz 9 $^1$H NMR spectra for oligophenoxyacetamides 2-6.
Figure 13:
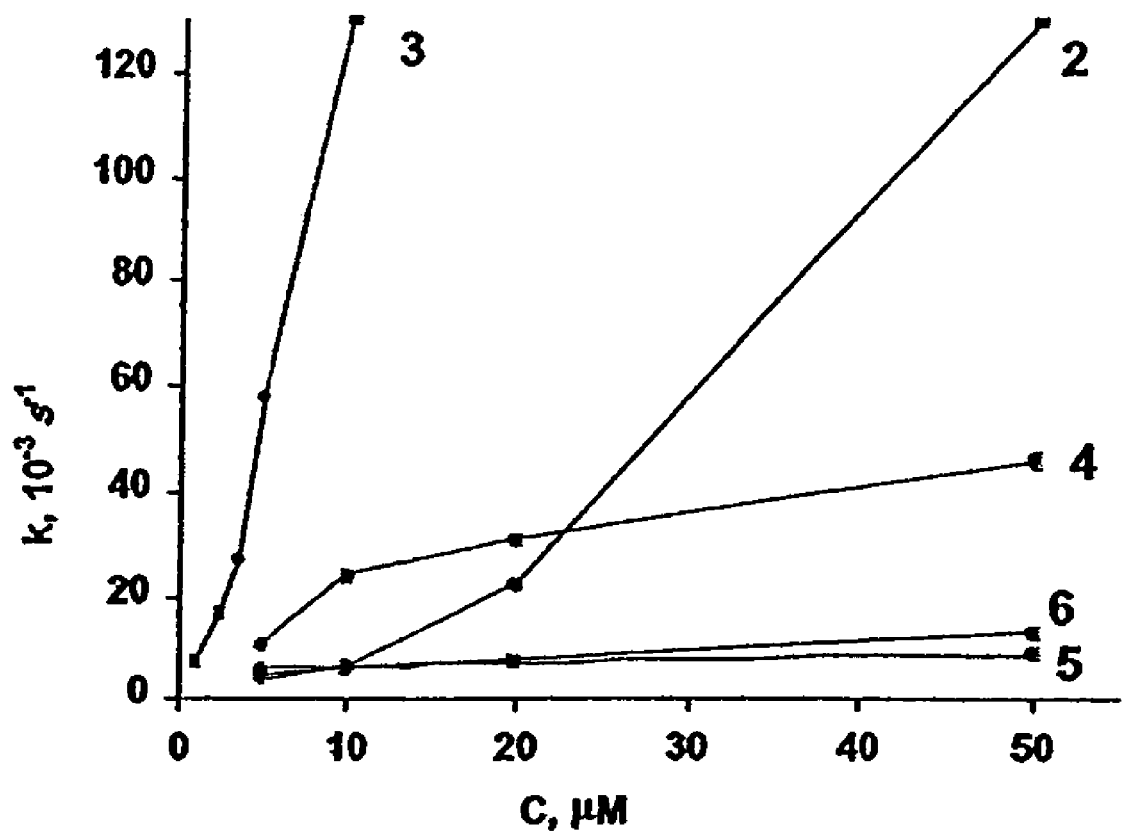
FIG. 13 illustrates dependence of the pseudo-first order initial rate constants on the concentrations of the ionophore 2-6. Each point on the plot represents a pH-stat fluorimetric experiment (HTPS emission is monitored at 510 nm with excitation at 403 and 460 nm, EYPC LUV'S (1.9 mL of LUV's suspension, 500.mn.M of EYPC. 10 mM sodium photosphate, pH 6.4, 100 mM NaCl inside, and outside) with the following time events: 20 s-20 .mu.L of DMSO solution of the compound of interest at the appropriate concentration is added (compounds are denoted by the colored legend), 60 s-21 mL of 0.5 M NaOH is injected, 500 s·−40 .mu.L of 5° n aqueous Triton X100 is injected). Color code for traces denotes application of: −2; −3; −4; −5; −6. The rate constants values calculated as described in the Fluorimetric Transport Assays section below.
Figure 14A:
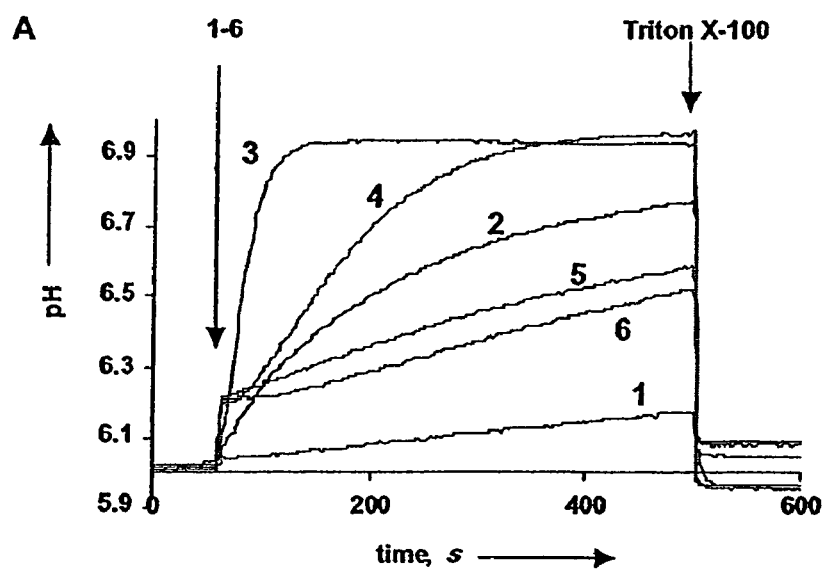
FIG. 14(A) illustrates alkalinization of the vesicular aqueous compartment upon application of 1-6 to a suspension of NaCl-containing vesicles in isosmomolar Na2SO4 buffer Concentration of 1-6 in the vesicular suspension was 20 .mu.M or 4:100 ligand to lipid ratio. Color code for traces denotes application of −1; −2; −2; −4; −5; −6.
Figure 14B:
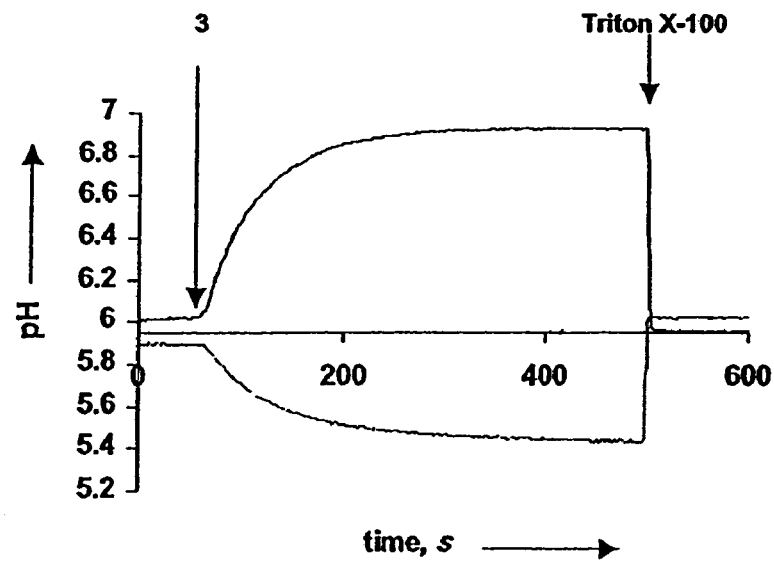
FIG. 14(B) illustrates alkalinization (upper trace) and acidification (lower trace) of the vesicular aqueous compartment upon injection of 3 (final concentration 5 .mu.M or 1:100 ligand to lipid ratio) to a suspension of NaCl-containing vesicles in isosmomolar Na2SO4 buffer (upper trace) and to a suspension of Na2SO4-containing vesicles in isosmomolar NaCl buffer (lower trace). Liposomes were lysed with Triton X-100 at the end of each experiment.
Figure 15A:
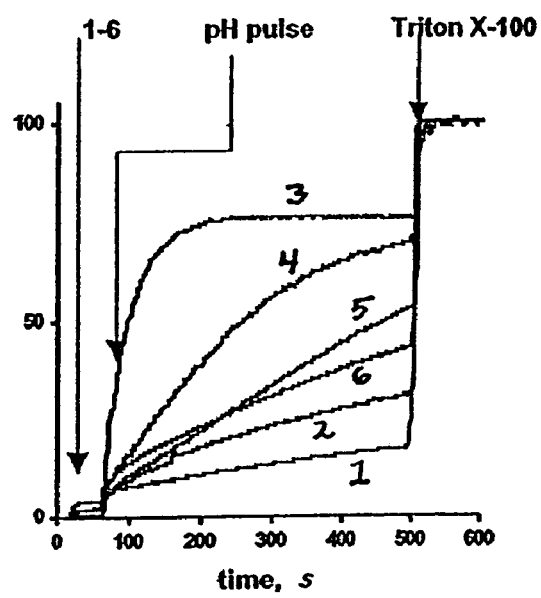
FIG. 15(A) and FIG. 15(B) illustrates liposome pH-stat transport assays with 1-6. Suspension of EYPC LUVs (500 .mu.M of lipid) containing the pH-sensitive dye pyranine (ex 405 and 460 nm, em 510 nm) in a phosphate buffer was used (10 mM NanH3-nPO4, n=1.2, pH 6.4, 100 mM NaCl inside and outside). Time events: 20 s:20 .mu.L of (A) 0.5 mM or (B) 2.0 mM solution of 2-6 in DMSO added to give 1:100 or 4:100 transporter lipid molar ratios respectively, 60 s:21 .mu.L of 0.5 M NaOH is added, 500 sec: 40 .mu.L of 5% Triton X-100 is added. Numbers in plots denote application of: −1, −2, −3, −4, −5, −6.
Figure 15B:
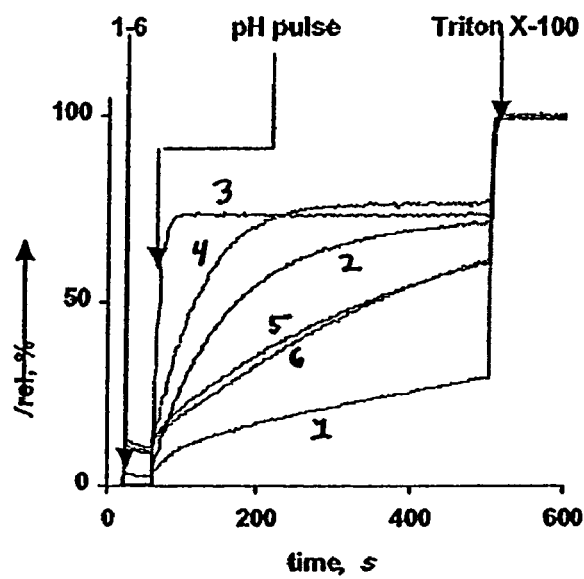
Figure 16:
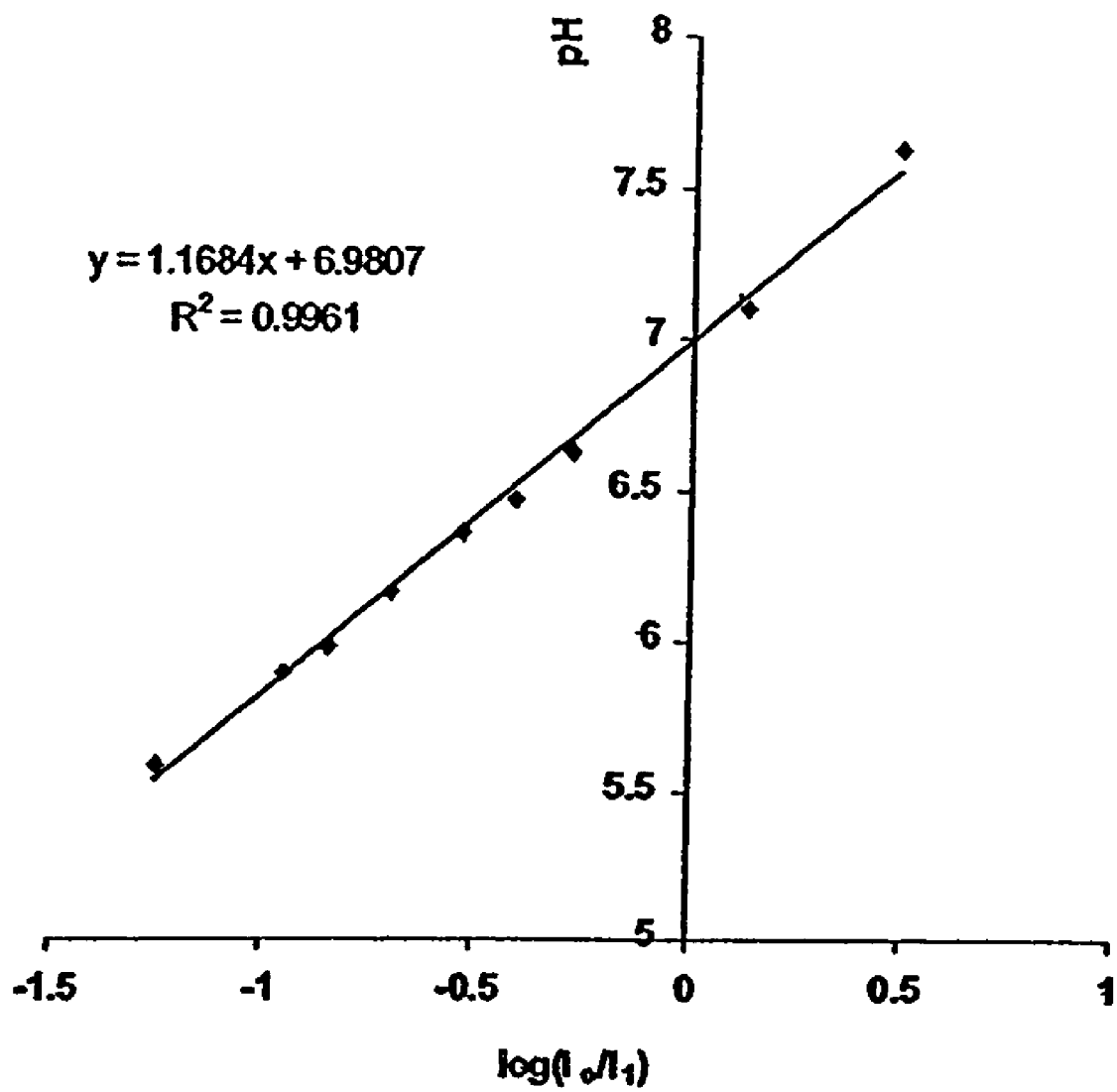
FIG. 16 illustrates calibration plot relating the HPTS emission intensity to a pH of the solution.

The voltage-clamp assay was conducted using a setup with two chambers, each filled with an electrolyte solution and separated by a BLM. After voltage was applied across the membrane, a solution of 2 was added to one of the chambers. Subsequent current across the membrane was attributed to ion transport mediated by 2, since control experiments wit DMSO solvent were negative. Typical current recordings are shown in FIG. 9a. The abrupt changes in current intensity (events) are consistent with an ion channel mechanism. The relatively long-lasting open states indicate that channels formed by calixarene tetrabutylamide 2 are stable.

Analysis of 480 events gave a distribution of conductance levels (50 pS-2 nS) centered near 100 pS. We attribute the various conductivity levels to formation of different self-assembled channel structures. One explanation for different assemblies formed by 2 is competition of calix[4]arene amides with water for Cl$^-$ binding, as revealed in the two different crystal structures for 1-HCl complexes. While one can only speculate about the structure of the active species, the experiments clearly indicate that calixarene 2 can form ion channels.

Calix[4]arene tetrabutylamide 2 forms voltage-dependent channels in HEK-293 cell membranes. Patch-clamp recordings in a whole-cell configuration revealed that extracellular application of 2 to HEK-293 cells caused current across the cell membrane at holding potentials of +120 mV (3 of 15 cells actually responded at +80 mV, whereas the other cells responded at +120 mV). Importantly, this current was observed only when the cells were suspended in NaCl buffer. Replacement of NaCl buffer with isosmotic Na glutamate or $Na_2SO_4$ resulted in no current across the membrane at holding potentials between −120 and +120 mV. These results lend further credence to the Cl$^-$ selectivity of ion channels formed from calix[4]arene tetrabutylamide 2.

Calixarene tetrabutylamide 2 could be washed out from the cell membrane. After 1.5 min of lavage, the current returned to the baseline and no further response at +120 mV was observed without further addition of 2. These data indicate that application of 2 did not damage the cell membrane. Subsequent reapplication of 2 resulted in a shortening of the delay prior to the response. One explanation for this phenomenon is that washing did not completely remove 2 from the cell membrane. Instead, inactive aggregates of 2 may remain. These membrane-retained "seeds" may then accelerate formation of new ion channels upon reapplication of the compound.

Calix[4]arene 1,3-alt tetrabutylamide 2 binds HCl and forms ion channels in lipid bilayer membranes. This is a rare example of a synthetic, non-peptide ion channel showing an anion dependence. We attribute the HCl binding and transport activity of 2 to the calixarene's three-dimensional structure, its hydrophobicity and the amide side chain's substitution pattern. Alteration of any of these features results in a selectivity switch from anions to cations (compound 3) or to loss of transport activity (compounds 1 and 4). Ion transport provided by 2 proceeds via either an $H^+/Cl^-$ symport or a $Cl^-/OH^+$ antiport mechanism. Compound 2 can regulate $H^+$ and $Cl^-$ gradients across the membrane. Two crystal structures demonstrate that the calix[4]arene 1,3-alt tetraamide motif is capable of forming chloride ion channels.

Experimental Section $^1$H NMR spectral were recorded on a Bruker DRX400 instrument at 400 130 MHz. Chemical shifts are reported in ppm relative to the residual solvent peak. The $^{13}$C NMR spectra were recorder at 100.613 MHz and chemical shift values are reported in ppm relative to the solvent peak. Mass spectra were recorded on a JEOL SX-102A magnetic sector mass spectrometer using fast atom bombardment. Fluorimetric experiments were done on an SLM Aminco (Aminco Bowan Series 2) Luminescence Spectrometer. Vapor pressure osmometry (VPO) was performed on a Wescot 5520. Vapro instrument. Solution pH was monitored with an Orion pH-meter, model 420A, with a Ag/AgCl pH-sensitive electrode. Chromatography was performed using 60-200 mesh silica from Baker. Thin-layer chromatography was performed in Kieselgel 60 F254 and Uniplate Silica Gel GF silica-coated glass plates and visualized by UV. HPLC analysis was performed on a Shimadzu LC-10AS liquid chromatograph with a Shimadzu SPD. 10 A UV-Vis detector set to 254 nm. A C-18 silica column was used as a stationary phase, and 1:1 $CH_3CN$:0.1% aqueous TFA was the mobile phase. Chemicals and solvents were purchased from Sigma, Fluka. Aldrich, or Acros. EYPC and cholesterol were purchased from Avanti Polar Lipids.

Synthesis. Calix[4]arene Tetramethylamide 1. Calix[4]arene tetramethylamide 1 was synthesized as described in footnote 1.

1-HCl crystals: (a) Calix[4]arene tetramethylamide 1 (15 mg) was dissolved in 1.5 mL of THF:12 M HCl (95:5). The solution slowly evaporated to give an oil precipitate that was dissolved in 2 mL of $CH_2Cl_2$. Slow evaporation afforded crystals of 1-HCl-3($H_2O$). (b) Calix[4]arene tetramethylamide 1 (15 mg) was dissolved in 2 mL of $CH_2Cl_2$, and then 1 mL of 6 M aqueous HCl was layered over the organic solution. A white emulsion in the organic layer occurred immediately. Crystals of 1-HCl-$H_2O$—$CH_2Cl_2$ formed at the aqueous-organic interface after several days.

Calix[4]arene tetrabutylamide 2, (a) To a suspension of tetrakis (carboxymethoxy)-p-H-calix[4]arene 1.3-alt (700 mg, 1.07 mmol) in 30 ML of benzene was added 2 mL of thionyl chloride 27.4 mmol 6.4 equiv per COOH group). The reaction mixture was stirred at reflux for 2.5 h, the solvent was evaporated under reduced pressure, and residual $SOCl_2$ was removed by coevaporation with benzene. IR spectroscopy indicated conversion of the carboxylic acid groups to acid chlorides. The acid chloride was used immediately without purification. (b) To a solution of the acid chloride in 30 mL of dry $CH_2Cl_2$ were added 3 mL of triethylamine (21.5 mmol, 5 eqiv) and 3 mL of butylamine (30.4 mmol, 7.1 equiv), the reaction mixture was stirred overnight at room temperature and washed with water and 0.1 N HCl and the resulting material was purified by column chromatography (silica gel, MeOH: $CH_2Cl_2$ 4.96) to give 814 mg (0.93 mmol, 87% yield) of 2 as a white solid $^1$H NMR (CDCl$_3$, 25° C.)δ: 7.00 (d, J=7.5 Hz 8 ArH), 6.73 (t, J=7.5 Hz, 4 H ArH), 6.26 (t, J=6.2 Hz, 4 H, CONH), 4.05 (s, 8 H, ArOCH$_2$CO), 3.58 (s δ: H ArCH$_2$Ar), 3.41 (m, 8 H, ArOCH$_2$CONHCH$_2$CH$_2$CH$_3$), 1:66)M, 8 H Ar—OCH$_2$—CO—NH—CH$_2$—CH$_2$—CH$_3$), 1.54 (m, 8 H, ArOCH$_2$CONHCH$_2$CH$_2$CH$_3$) 1.06 (t, J=7.5 Hz, 12 H ArOCH$_2$CONHCH$_2$CH$_2$CH$_3$), $^{13}$C NMR (CDCl$_3$, 25° C.)δ: 167.7, 154.3, 133.9, 131.2, 122.1, 70.1, 38.8, 36.2, 32.5, 20.2, 13.9, FAB MS ([M+H]$^+$): 877.5, called for $C_{52}H_{69}N_4OH_8$ 877.50.

Calix[4]arene Octabutylamide 3. Tetrakis(carboxymethoxy)-p-H-calix[4]arene (423 mg, 0.65 mmol) was activated with thionyl chloride as described for 2. To a solution of the acid chloride in 30 mL of dry methylene chloride were added 2 mL of triethylamine (14.3 mmol, 5.5 equiv) and 3 mL of butylamine (17.8 mmol, 6.8 equiv). The reaction mixture was stirred overnight at room temperature and then washed with water and 0.1 N HCl, evaporated to dryness under reduced pressure, and submitted to column chromatography (silica gel, MeOH:$CH_2Cl_2$ 6.94) to give 3, contaminated with its Na$^+$ complex (determined by $^1$H NMR). Repeated washing of this material with deionized water gave 443 mg of 3 (0.40 mmol, 62%) as a white solid. $^1$H NMR (CDC$_3$ 25° C.) δ: 7.16 (d, J=8.1 Hz 8 ArH), 6.67 (t, J=7.7 Hz, 4 H ArH), 4.41 (s, 8 H, ArOCH$_2$CO), 3.56 (S 8 H ArCH$_2$Ar), 3.41 (t, J=7.7 Hz 8 H, ArOCH$_2$CON (CH$_2$)$_2$,), 3.23 (t, J=7.7 Hz 8 H ArOCH$_2$—CON(CH$_2$)$_2$), 1.63-1.52 (m, 16 H, ArOCH$_2$CON(CH$_2$CH$_2$CH$_3$)$_2$), 0.95 (t, J=7.3 Hz, 12 H ArOCH$_2$CON(CH$_2$CH$_2$CH$_2$CH$_2$CH$_3$)$_2$), 0.92 (t, J=7.3 Hz, 2 H ArOCH$_2$CON(CH$_2$CH$_2$CH$_2$CH$_3$)$_2$).

$^{13}$ C NMR (CDCl$_3$, 25° C.) δ: 167.6, 155.39, 133.3, 129.5, 23.0, 71.7, 47.0, 45.5, 33.6, 31.2, 29.7, 20.2, 20.0, 13.9, 13.7, FAB MS ([M+H]$^+$): 1101.75 called for $C_{68}H_{10}N_4O_8$ 1101.75

N-Butyl-2-phenoxyacetamide 4, Phenoxyacetic acid (2 g, 13.15 mmol) was activated with SOCl$_2$ (3 mL, 41.1 mmol, 3 equiv) in 50 mL of dry benzene using the procedure described for 2. To a solution of the acid chloride in 30 mL of dry methylene chloride were added 3 mL of Et$_3$N (21.5 mmol, 1.6-fold excess) and 3 mL of BuNH$_2$ (30.4 mmol, 2.3-fold excess). The reaction mixture was stirred overnight at room temperature, the solvent was evaporated to dryness under reduced pressure, and the resulting oil was dried under high vacuum. Purification by column chromatography (silica gel, MeOH:$CH_2Cl_2$ 2:98 vv) gave 2.43 g (11.71 mmol, 89%) of 4 as crystalline solid. $^1$H NMR (CDCl$_3$ 25°

C.) δ: 7.32 (dd, J=8.0, 7.2 Hz 2 H, Ar—H), 7.02 (t, J=7.2 Hz, 1 H ArH), 6.91 (d, J=8.0 Hz, 2 H, ArH), 6.57 (bs. 1 H, NH), 4.48 (s, 2 H ArOCH$_2$CO_, 3.34 (q, J=6.8 Hz, 2 H, NHCH$_2$CH$_2$CH$_3$), 1.33 (m, 2 H NHCH$_2$CH$_2$CH$_3$), 0.91 (t, j=7.2 Hz, 3 H NHCH$_2$CH$_2$CH$_3$), $^{13}$C NMR (CDCl$_3$, 25° C.) δ: 168.0, 157.1, 129.7, 122.0, 114.5, 67.3, 38.7, 31.5, 19.9, 13.6 MS (FAB)([M]$^+$): 207.3 called for C$_{12}$H$_{17}$NO$_3$ 207.13.

Liposome Preparation. EYPC HPTS-Containing LUVs, egg yolk 1-α-phosphatidylcholine (EYPC, 60 mg, 79 pM) was dissolved in a CHCl$_3$MeOH mixture, the solution was evaporated under reduced pressure, and the resulting thin film was dried under high vacuum for 2 h. The lipid film was hydrated in 1.2 mL of phosphate buffer (10 mM sodium phosphage, pH=6.4, 75-100 mM MX, M=Na$^+$, K$^+$, Cs$^+$, X=Cl$^+$, SO$_4^{2-}$) containing 10 μM HPTS (pyranine 8-hydroxypyrene-1,3,6-trisulfonic acid trisodium salt) for 2 h. The LUV suspension (1 mL) was submitted to high-pressure extrusion at room temperature (2) extrusions through a 0.1 μM polycarbonate membrane afforded LUVs with a diameter of 100 nm). The LUV suspension was separated from extravesicular dye by size exclusion chromatography (SEC) stationary phase: Sephadex G-10, mobile phase:phosphate buffer) and diluted with the same phosphate buffer to give a stock solution with a lipid concentration of 11 mM (assuming 100% of lipid was incorporated into liposomes).

EYPC Calcein-Containing Vesicles: Calcein (224.1 mg, 0.36 mmol) was suspended in 3 mL of phosphate buffer (100 mM NaCl, 10 mM sodium phosphate, pH 6.4). The pH of the solution was adjusted to 6.4 with a 7.4 M NaOH-containing phosphate buffer, at which point all the calcein was dissolved to give a 120 mM solution of the dye. The molality of the extravesicular buffer was adjusted to equal that of the calcein-containing solution with 1 m NaCl. Osmomolality was determined by VPO. A thin film was prepared from 60 mg of EYPC (79 μM) as described above. The lipid film was hydrated in 1.2 mL of the calcein buffer. During hydration, the suspension was submitted to five freeze-thaw cycles (dry ice in acetone, water at room temperature) and then submitted to high-pressure extrusion (2) extrusions through a 0.1 μm polycarbonate membrane afforded LUVs with an average diameter of 100 nm). Calcein-containing LUVs were separated from extravesicular dye by SEC stationary phase: Sephadex G-25, mobile phase: extravesicular buffer with adjusted molality.

Unequally Loaded Vesicular Suspensions (intra- and extravensicular buffers are different). The molality of the extravesicular buffer was adjusted to that of intravesicular buffer by addition of a 1 M solution of the appropriate salt in phosphate buffer (molality of solutions was monitored by VPO). The pH of extravesicular buffer was adjusted to that of intravesicular buffer by addition of 1 M HCl or 1 M NaOH solution (monitored by pH meter).

Fluorimetric Transport Assays. pH-Assisted Transport Assays. Typically, 100 μL of HPTS-loaded vesicles (stock solution) was suspended in 1.85 mL of the corresponding buffer and placed into a fluorimetric cell. HPTS emission at 510 nm was monitored with excitation wavelengths at 403 and 460 nm simultaneously. During the experiment, 20 μL of a 0-10 mM THF solution of the compound of interest was added through an injection port, followed by injection of 21 μL of 0.5 M aqueous NaOH. Addition of the NaOH caused a pH increase of approximately 1 pH unit in the extravesicular buffer. Maximal changes in dye emission were obtained at the end of each experiment by lysis of the liposomes with detergent (40 μL of 5% aqueous Triton x100). The final transport trace was obtained as a ratio of the emission intensities monitored at 460 and 403 nm and normalized to 100% of transport. Pseudo-first-order rate constants were calculated form slopes of the plot of ln([H$^+$ins]–H$^+$out) versus time, where (H$^+$ins) are the intravesicular and extravesicular proton concentrations. The H$^+$ out was assumed to remain constant during the experiment, while (H$^+$ins) values were calculated for each point from the HPTS emission intensities according to the calibration equation pH=1.1684×log(I$_0$/I$_1$)=6.9807. The absolute values for rate constants varied depending on the age of the vesicular solution and the actual stock solution of liposomes used. Ratios between absolute values of rate constants obtained from experiments on the same batch of liposomes, however, did not vary significantly.

Calcein-Release Assay. Calcein-loaded vesicles (100 μL of the stock solution), filled with a saline phosphate buffer (10 mM sodium phosphate, pH 6.4, 100 mN NaCl), were suspended in 1.85 mL of an isoosmotic phosphate sulfate buffer (10 mM sodium phosphate, pH 6.4$^-$75 mM (Na$_2$SO$_4$) and placed into a fluorimetric cell. HPTS emission at 510 nm was monitored with excitation wavelengths at 403 and 460 nm simultaneously. During the experiment, 20 μL of a 0-500 μM THF solution of the compound of interest was added through an injection port. Intravesicular pH values were obtained as a function of the ratio of HPTS emission intensities at 510 nm, when excited at 403 and 460 nm. The calibration was performed by measuring the HPTS emission intensities and the pH values of a 470 pM HPTS solution in 10 mM phosphate buffer containing 100 mM NaCl (pH was varied in the range of 5.6 through 7.6 addition of 0.5 M NaOH or 0.5 HCl). The calibration equation obtained pH=1.1684×log)I$_0$/I$_1$)+6.9807, r and l$_1$ is emission intensity with excitation at 403 nm) was applied to convert the emission intensities into pH values. At the end of experiment, the aqueous compartment of liposomes was equilibrated with extravesicular solution by lysis of liposomes with detergent (40 μL of 5% aqueous Triton x100).

Electrophysiological Recordings. Patch-Clamp Experiments. HEK 293 cells, plated in 100-nm dishes containing 10 mL of the growth media were maintained at 37° C. with 5% CO$_2$ in the incubator. Growth medium for HEK 293 cells was minimum essential medium supplemented with 10% fetal bovine serum, 100 U mL penicillin and 100 μg/mL streptomycin. Electrophysiological recordings were performed in the whole-cell configuration of the patch-clamp technique using a DAGAN 8900 amplifier (Dagan Corp., Minneapolis, Minn.). The patch electrodes, pulled from borosilicate class capillaries, had resistance of 3-4 MΩ when filled with internal solution containing (in mM): CsCl 110: tetraethylammonium chloride, 20; MgATP. 5:EGTA. 14: HEPES, 20 and titrated to pH 7.4 with CsOH. Approximately 90% of electrode resistance was compensated electronically, so that effective series resistance was less than 1 MΩ. HEK cells were used for experiments 2 to 4 days after plating the cells on the cover sips. Generation of the voltage-clamp protocols and data acquisition were carried out using PCLAMP software (Axon instruments, Inc., Burlingame, Calif.). Sampling frequency was 0.5-2.0 kHz, and current signals were filtered at 10 kHz before digitization and storage. All experiments were performed at room temperature (23-25° C.). Cells selected for recordings had a capacitance of 25-35 pF. Cells plated on plastic cover slips 915 mm round thermanox, Nunc, Inc., Napierville, Ill.) were transferred to an experimental chamber mounted on the stage of an inverted microscope (Diaphot, Nikon, Nagano, Japan) and were bathed in a solution containing (in mM):NaCl, 137:CaCl$_2$, 2; KCl. 5.4; HEPES, 10; glucose, 10:glucose, 10; MgCl$_2$, 1 (pH 7.4 adjusted with NaOH). The experimental chamber was constantly perfused at a rate of about 1 mL/min with a control bathing solution. In solutions buffered on the cell under recording KCl was omitted and in some experiments NaCl was replaced by isoosmotic amounts of $Na_2SO_4$ or Na glutamate. Servo-controlled miniature solenoid valves were used for rapid switching between control and test solutions (delay in solution change was <20 ms). Compound 2 was dissolved in DMSO, and DMSO was added in an equal amount to the control and test solutions.

Voltage-Clamp Experiments. Bilayer membranes were made from monolayers of diphytanoylphospatidylcholine (DPhPC) using the method of Montal and Mueller. Recordings were made under voltage-clamp conditions using calomel electrodes with saturated KCl bridges. Solutions consisted of 1 M KCl, 1 mM $MgCl_3$, 5 mM HEPES, pH 7.0. The voltage was applied from the trans side of the lipid membrane. Once calixarene tetrabutylamide 2 was incorporated into the lipid, the current through the membrane was recorded using both a chart recorder and directly digitized and stored as a computer file. The conductance values were calculated by dividing the current by the applied voltage. The events were grouped into conductance ranges of equal magnitude for the purpose of showing the distribution of recorded conductances.

Supporting Information Available: Crystallographic data including diffractometer and refinement data, final coordinates, bond lengths and angles, hydrogen bond lengths and angles, and anisotropic displacement values (PDF). Crystallographic data is also available in cif format. This material is available free of charge at http://pubs.acs.org.

Although trimer 3 transports both $Cl^-$ and $H^+$ into sulfate-loaded liposomes suspended in $Cl^-$ buffer, the overall process is not electrically silent. Nyu monitoring this transmembrane potential using the potential-sensitive dye safranin O revealed the formation of stable negative charge inside liposomes ($Na_2SO_4$ inside, NaCl outside, safranin O outside) with 2 minutes after application of 1 mol % trimer. The magnitude of the transmembrane potential induced by 3 under an inwardly directed $Cl^-$ gradient is comparable to that generated by 0.12 mol % valinomycin in liposomes with an outwardly direct $K^+$ gradient (100 mM KCl inside, 100 mM NaCl outside). The lower two traces in FIG. 2 verify that trimer 3 and valinomycin are functionally orthogonal. That is, trimer 3 created transmembrane potential under conditions where valinomycin cannot create a potential and vice versa. Thus, trimer 3 was observed to induce a stable potential inside liposomes due to the formation of a transmembrane anionic gradient. Moreover, this compound is of particular advantage in forming transmembrane anionic gradients, due to its high activity at low µM concentrations.

The compounds of the present invention are advantageously used to form anion channels in either mammalian cell membranes or in exogenous phospholipid membranes, and, particularly, bicarbonate or chloride anion channels, most particularly chloride anion channels.

For example, any of the compounds of the present invention may be used to form chloride ion channels in a mammal, preferably a human, for the purpose of treating a disease or condition attended by either the absence or defective function of chloride ion channels. Thus, the compounds of the present invention may be used advantageously in the treatment of CF.

As noted above, the present compounds may also be used for bicarbonate anion transport across lipid bilayers. This is advantageous as bicarbonate anions is important in many biochemical reactions. For example, bicarbonate anion is important in enzymatic carboxylation reactions generally, and specifically, with carboxylation of pyruvate, acetyl-Co A, propionyl-Co A, β-methylcrotonyl-Co A, geronyl-Co A, and urea.

Additionally, bicarbonate anion is important in intracellular pH regulation. Thus, the present invention may be used to provide enhanced in vivo enzymatic carboxylation and regulation of intracellular pH, if desired.

The compounds of the present invention may be administered in any manner, however, they are preferably administered either intravenously, topically or by inhalation. If administered intravenously, they may be administered in a suitable carrier, such as sterile saline or dextrose 5% saline solution. Generally, a solution concentration of from 0.01% to 5% by weight is used, however, greater or lesser concentrations may be used as needed. Further, it is generally desirable to administered a total amount of amide compound or compounds of from about 10 µg to 100 mg per day.

If administered topically, the compounds of the present invention may be formulated in any conventional topical base which is applicable and absorbable on mammalian, or preferably human skin. Generally, lotion or ointment may be used which contains a secondary amide concentration of from 0.01% to 50% by weight based on the total weight of the lotion or ointment. Preferably, the lotion or ointment is about 0.1% to 20% by weight of the secondary amides of the present invention based on the total weight. Further it is generally desirable to administer a total amount of amide compound or compounds of from about 10 µg to 100 mg per day.

Most preferably, however, the compounds of the present invention are formulated for inhalation in a vaporizer or nebulizer. Generally, any conventional carrier formulation may be used in the vaporizer or nebulizer to introduce the compounds of the present invention into the bronchial passage and lungs of the mammal, particularly human, being treated. Generally, a carrier formulation may be used which contains an amide concentration of form 0.01 % to 5% by weight based on the total weight of the carrier formulation. Further it is generally desirable to administer a total amount of amide-functionality compound or compounds of from about 10 μg to 500 mg per day.

As used herein, the term "nebulizer" is used to refer to an inhalation device that is used to deliver a dose of a pharmaceutical composition to the lungs via the bronchial passages. The term "vaporizer" is used to refer to a humidifier device that delivers an amount of a pharmaceutical composition to a room or confined space for intake by breathing. As used herein, the term "nebulizer" is understood to mean all manners of metered-dose inhalers, including dry powder inhalers; and aerosol holding chamber devices and nebulizers.

Generally, the vaporizable compositions of the present invention will include one or more of the monomers or polymers of the present invention in a suitable carrier. However, any additional substances used in conventional CF treatment therapies may be used such as antibiotics and proteolytic enzymes, including amylases and lipases. Additionally DNase enzymes may also be included.

Any antibiotic conventionally used in the treatment of secondary bacterial infections with bronchial disease or conditions may be used in any of the compositions of the present invention. Of particular note, however, is tobramycin in solution form. This antibiotic is known to be highly effective against lung infections when administered by inhalation.

However, other antibiotics may be used including arythromycin and azithromycin, for example. Any of the antibiotic formulations of U.S. Pat. No. 6,576,224 or U.S. Pat. No. 6,387,886 may be used with modifications to include one or more of the compounds of the present invention. U.S. Pat. No. 6,576,224 and U.S. Pat. No. 6,387,886 are each incorporated herein in their entirety.

As the compounds of the present invention are slightly soluble in water, it is generally preferred that an organic or fatty solvent be used to assist in the solubilization or emulsification of the compounds if they are to be delivered in a liquid state. Any conventionally used organic or fat-solubilized solvents for nebulizers may be used.

Additionally, as noted above each "core aromatic" ring contains at least one axyacetamide side chain. The term "core aromatic" ring refers to the aromatic rings which are part of the backbone of oligo compounds or which are the backbone of the macrocyclic structure, such as a calixarene structure.

The term "oxyacetamide-based" as used herein means a group of the formula:

$$-O-CH_2-C(O)-NH-R$$

wherein R is a substituent as defined above. It is preferred, however, that R be lower alkyl of 1 to 8 carbon atoms, preferably from 1 to 6 carbons, and most preferably from 2 to 5 carbons. The oxyacetamide-based group is, for example, methyl oxyacetamide, ethyl oxyacetamide, propyl oxyacetamide, n-butyl oxyacetamide, n-pentyl oxyacetamide or n-hexyl oxyacetamide, where X corresponds to $C_1$, $C_2$, $C_3$, $C_4$, $C_5$ and $C_6$, respectively.

In accordance with the present invention, it is particularly effective to administer the oligomers and polymers of the present invention by nebulizer. Any nebulizer system may be used to treat asthma, but varying the composition in the nebulizer. Nebulizers are advantageous as they generate small droplets that reach the minute airways of the lungs. In accordance with the present invention, antibiotics may be used in the nebulizer composition to treat lower airway bacterial infections in patients having CF.

Of course, the composition of the present invention may, in serious cases, be administered in a mist tent. A mist tent is a plastic enclosure which is filled with mist from a vaporizer. If necessary, the treatment may also include humidification, whereby water vapor is also released into the tent to humidify the airway membranes of a patient to prevent the membranes from drying out.

As examples of nebulizer delivery systems which may be used, the following U.S. patents are noted, and are incorporated herein by reference in the entirety: U.S. Pat. No. 5,524,613, which pertains to a powdered drug inhaler with multiple reservoirs for different pharmaceuticals; U.S. Pat. No. 5,511,538, which pertains to a mechanical atomizer for a liquid mist; U.S. Pat. No. 5,433,191, which pertains to a pump spray device; U.S. Pat. No. 5,378,233, which pertains to a single or dual dose liquid medication auto-injector; and U.S. Pat. No. 5,287,850, which pertains to a pressurized air-powered dry powder inhaler.

If desired, the compounds and compositions of the present invention may also be administered as drops from a nasal dispenser using any conventional dispensers and carrier systems.

However, it is explicitly recognized that the dosages and concentrations noted herein for medicinal use may be modified pursuant to trained medical observations. For example, higher concentrations and use frequent dosages may be employed if, in the estimate of a medical professional, such increases are warranted.

Finally, it is specifically noted that due to the $H^+$ $CL^-$ symport activities of the present compounds, they may also be used advantageously in the treatment of cancer.

This application claims priority to provisional application S. N. 60/445,160, which is incorporated herein in the entirety.

Having described the present invention, it will now be apparent that many changes and modifications may be made to the above embodiments without departing from the spirit and the scope of the present invention.

What is claimed is:

1. A compound having the formula (I):

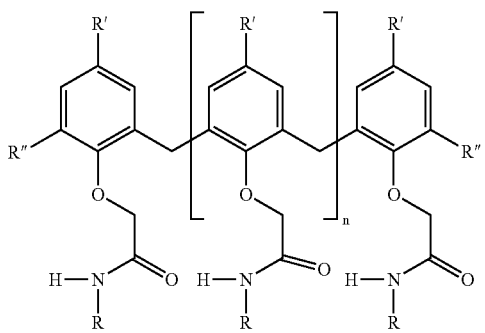

wherein:
- n is an integer of from 0 to 12;
- R is acyclic alkyl of 3 to 12 carbons, cyclic alkyl of 5 to 12 carbons, cyclic alkyl of 5 to 12 carbons, aromatic group, an amino acid, or peptide groups;
- R' is —H, acyclic alkyl of 1 to 12 carbons, cyclic alkyl of 5 to 12 carbons, cyclic alkyl of 5 to 12 carbons, aromatic, heterocyclic or peptide groups; and
- R" is —H, acyclic of 1 to 12 carbons, cyclic alkyl of 5 to 12 carbons, aromatic, heterocyclic or peptide groups.

2. The compound of claim 1, wherein n is an integer of from 0 to 8.

3. The compound of claim 2, wherein n in the formula (I) is 2.

4. The compound of claim 1, wherein n is an integer of from 2 to 6.

5. A pharmaceutical composition comprising one or more of the compounds of claim 1, and a pharmaceutically-acceptable carrier, said one or more compounds being in an amount effective to transport anions across mammalian cell membranes.

6. The pharmaceutical composition of claim 5, which is in a form of a lotion or ointment for topical administration.

7. The pharmaceutical composition of claim 5, which is in a form of a compressed liquid or dry powder for administration by inhalation.

8. The pharmaceutical composition of claim 7, which is in the form of a compressed liquid for administration by inhalation.

9. The pharmaceutical composition of claim 8, which further comprises tobramycin.

10. A pharmaceutical composition comprising one or more of the compounds of claim 3, and a pharmaceutically-acceptable carrier, said one or more compounds being present in an amount effective to transport anions across mammalian cell membranes.

11. The pharmaceutical composition of claim 10, which is in a form of a lotion or ointment for topical administration.

12. The pharmaceutical composition of claim 10, which is in a form of a compound liquid or dry powder for administration by inhalation.

13. The pharmaceutical composition of claim 12, which further comprises tobramycin.

14. A vaporizer comprising an effective amount of the composition of claim 5.

15. A vaporizer comprising an effective amount of the composition of claim 10.

16. A method of treating cystic fibrosis, which comprises administering an effective amount of one or more of the compounds of claim 1 to a mammal in need thereof.

17. The method of claim 16, wherein said one or more compounds are administered by inhalation.

18. The method of claim 17, which further comprises an antibiotic.

19. The method of claim 16, wherein said mammal is a human.

20. The method of claim 16, wherein said one or more compounds are oligomers administered by nebulizer as a liquid mist.

21. A method of forming chloride ion channels in mammalian cell membranes, which comprises administering an effective amount of one or more of the compounds of claim 1 to a mammal in need thereof.

22. The method of claim 21, wherein said mammal is a human.

23. A compound comprising four phenyl rings, each being bonded through a methylene linkage, each ring having at least one oxyacetamide based said chain, and said compound having a 1, 3 alt configuration, wherein the oxyacetamide-based side chain has the formula —O—$CH_2$—C(O)—NHR, wherein R is $C_3$—$C_8$-alkyl.

24. The compound of claim 23, wherein R is $C_4$-alkyl.

25. A pharmaceutical composition comprising one or more of the compounds of claim 23, and a pharmaceutically acceptable carrier, said one or more compounds being in an amount effective to transport anions across mammalian cell membranes.

26. A vaporizer comprising the composition of claim 25.

27. The compound of claim 1, wherein said R' is —H or $C_1$—$C_{12}$ alkyl.

28. The compound of claim 1, wherein said R" is —H or $C_1$—$C_{12}$ alkyl.

29. The compound of claim 1, wherein said R is $C_3$—$C_5$ alkyl.

30. The compound of claim 1, wherein R is a peptide group of up to 10 amino acids.

31. The compound of claim 30, wherein the peptide of up to 6 amino acids.

32. The compound of claim 1, wherein R is an amino acid.

33. The compound of claim 1, wherein R is an aromatic group selected from the group consisting of phenyl and benzyl, which are each optionally substituted.

34. The compound of claim 29, wherein R is butyl.

35. The compound of claim 34, which is calix [4] arene tetrabutylamide-alt.

* * * * *